(12) United States Patent
Fryshman

(10) Patent No.: US 10,185,896 B2
(45) Date of Patent: Jan. 22, 2019

(54) INDUCTION SYSTEM FOR MOLD REMEDIATION

(71) Applicant: Bernard Fryshman, Brooklyn, NY (US)

(72) Inventor: Bernard Fryshman, Brooklyn, NY (US)

( * ) Notice: Subject to any disclaimer, the term of this patent is extended or adjusted under 35 U.S.C. 154(b) by 0 days.

(21) Appl. No.: 16/100,489

(22) Filed: Aug. 10, 2018

(65) Prior Publication Data

US 2018/0349745 A1 Dec. 6, 2018

Related U.S. Application Data

(63) Continuation-in-part of application No. 16/035,919, filed on Jul. 16, 2018, which is a continuation-in-part
(Continued)

(51) Int. Cl.
*G06K 9/00* (2006.01)
*G06K 9/62* (2006.01)
(Continued)

(52) U.S. Cl.
CPC ............ *G06K 9/6267* (2013.01); *A01H 1/025* (2013.01); *A01M 1/026* (2013.01); *A01M 1/06* (2013.01); *A01M 1/14* (2013.01); *A01M 1/20* (2013.01); *A01M 1/2094* (2013.01); *A01M 1/22* (2013.01); *A01M 1/226* (2013.01); *A01M 3/005* (2013.01); *A01M 3/007* (2013.01); *A01M 5/02* (2013.01); *A01M 5/04* (2013.01); *A01M 7/00* (2013.01); *A01M 99/00* (2013.01); *B64C 39/024* (2013.01); *B64D 1/18* (2013.01); *B64D 47/08* (2013.01); *G06K 9/00* (2013.01); *G06K 9/6256* (2013.01); *G06T 3/40* (2013.01); *G06T 7/0004* (2013.01); *G06T 7/0008* (2013.01); *G06T 7/62* (2017.01); *G06T 7/90* (2017.01); *H04N 5/225* (2013.01); *H04N 5/2252* (2013.01); *H04N 5/2253* (2013.01); *H04N 7/185* (2013.01); *B64C 2201/027* (2013.01); *B64C 2201/12* (2013.01); *G06K 2209/17* (2013.01); *G06T 2207/10024* (2013.01); *G06T 2207/10032* (2013.01); *G06T 2207/10056* (2013.01);
(Continued)

(58) Field of Classification Search
CPC combination set(s) only.
See application file for complete search history.

(56) References Cited

U.S. PATENT DOCUMENTS 8,275,413 B1 * 9/2012 Fraden .............. H04M 1/72522
455/344
9,877,783 B2 * 1/2018 van der Weide .. A61B 18/1815
(Continued)

*Primary Examiner* — Anand P Bhatnagar
(74) *Attorney, Agent, or Firm* — Bell & Manning, LLC

(57) ABSTRACT

A mold remediation system includes a processor and an electromagnetic radiation source in communication with the processor. The electromagnetic radiation source is configured to emit radiation to heat a ferromagnetic material in or adjacent to a wall board upon which mold is located. The system also includes a temperature sensor in communication with the processor. The temperature sensor is configured to detect a temperature of the wall board. The processor is configured to compare the temperature of the wall board to a desired temperature to perform mold remediation.

20 Claims, 9 Drawing Sheets

Related U.S. Application Data of application No. 15/956,083, filed on Apr. 18, 2018, now Pat. No. 10,043,263, which is a continuation-in-part of application No. 15/919,541, filed on Mar. 13, 2018, now Pat. No. 10,026,165, which is a continuation-in-part of application No. 15/802,814, filed on Nov. 3, 2017, now Pat. No. 9,965,850, and a continuation-in-part of application No. 15/654,390, filed on Jul. 19, 2017, now Pat. No. 9,852,362, which is a continuation-in-part of application No. 15/425,079, filed on Feb. 6, 2017, now Pat. No. 9,811,764, which is a continuation of application No. 15/153,621, filed on May 12, 2016, now Pat. No. 9,563,945, and a continuation-in-part of application No. 14/733,044, filed on Jun. 8, 2015, now Pat. No. 9,381,646, which is a continuation-in-part of application No. 14/505,430, filed on Oct. 2, 2014, now Pat. No. 9,053,528, which is a continuation-in-part of application No. 13/542,416, filed on Jul. 5, 2012, now Pat. No. 8,855,374.

(60) Provisional application No. 62/551,345, filed on Aug. 29, 2017, provisional application No. 62/183,591, filed on Jun. 23, 2015, provisional application No. 61/504,462, filed on Jul. 5, 2011.

(51) Int. Cl.

| | | |
|---|---|---|
| *A01H 1/02* | (2006.01) | |
| *B64D 1/18* | (2006.01) | |
| *B64C 39/02* | (2006.01) | |
| *H04N 7/18* | (2006.01) | |
| *A01M 7/00* | (2006.01) | |
| *H04N 5/225* | (2006.01) | |
| *G06T 7/00* | (2017.01) | |
| *A01M 3/00* | (2006.01) | |
| *A01M 1/22* | (2006.01) | |
| *A01M 1/20* | (2006.01) | |
| *A01M 1/14* | (2006.01) | |
| *A01M 1/06* | (2006.01) | |
| *A01M 1/02* | (2006.01) | |
| *A01M 5/04* | (2006.01) | |
| *G06T 7/62* | (2017.01) | |
| *G06T 7/90* | (2017.01) | |
| *B64D 47/08* | (2006.01) | |
| *G06T 3/40* | (2006.01) | |
| *A01M 5/02* | (2006.01) | |
| *A01M 99/00* | (2006.01) | |

(52) U.S. Cl.
CPC .............. *G06T 2207/20081* (2013.01); *G06T 2207/30128* (2013.01); *Y02A 50/375* (2018.01); *Y10S 901/01* (2013.01); *Y10S 901/09* (2013.01); *Y10S 901/40* (2013.01); *Y10S 901/41* (2013.01)

(56) References Cited

U.S. PATENT DOCUMENTS

| | | | |
|---|---|---|---|
| 9,891,110 B1* | 2/2018 | Pei | G01J 5/026 |
| 9,967,924 B2* | 5/2018 | Heczko | H05B 6/1245 |
| 2001/0019051 A1* | 9/2001 | Clothier | H05B 6/06 |
| | | | 219/622 |
| 2004/0081221 A1* | 4/2004 | Sandvoss | G01N 25/72 |
| | | | 374/130 |
| 2008/0014111 A1* | 1/2008 | Hedman | A01M 1/2094 |
| | | | 422/3 |
| 2008/0147056 A1* | 6/2008 | van der Weide | A61B 18/18 |
| | | | 606/33 |
| 2009/0000620 A1* | 1/2009 | Virr | A61M 16/1075 |
| | | | 128/203.27 |
| 2010/0024462 A1* | 2/2010 | Kamisako | A23L 3/3409 |
| | | | 62/331 |
| 2011/0064605 A1* | 3/2011 | Hedman | A01M 1/2094 |
| | | | 422/3 |
| 2011/0064607 A1* | 3/2011 | Hedman | A01M 1/2094 |
| | | | 422/5 |

\* cited by examiner

INDUCTION SYSTEM FOR MOLD REMEDIATION

CROSS-REFERENCE TO RELATED APPLICATIONS

The present application claims priority as a continuation-in-part application of U.S. patent application Ser. No. 16/035,919 filed on Jul. 16, 2018, which is a continuation-in-part of U.S. patent application Ser. No. 15/956,083 filed on Apr. 18, 2018, which is a continuation-in-part application of U.S. patent application Ser. No. 15/919,541 filed on Mar. 13, 2018, which is a continuation-in-part application of U.S. patent application Ser. No. 15/802,814 filed on Nov. 3, 2017, which claims priority to U.S. Patent App. No. 62/551,345 filed on Aug. 29, 2017. U.S. patent application Ser. No. 15/802,814 is also a continuation-in-part of U.S. patent application Ser. No. 15/654,390 filed on Jul. 19, 2017 (now U.S. Pat. No. 9,852,362), which is a continuation-in-part of U.S. patent application Ser. No. 15/425,079 filed on Feb. 6, 2017 (now U.S. Pat. No. 9,811,764), which is a continuation of U.S. patent application Ser. No. 15/153,621 filed on May 12, 2016 (now U.S. Pat. No. 9,563,945), which claims priority to U.S. Patent App. No. 62/183,591 filed on Jun. 23, 2015. U.S. patent application Ser. No. 15/153,621 is also a continuation-in-part of U.S. patent application Ser. No. 14/733,044 filed on Jun. 8, 2015 (now U.S. Pat. No. 9,381,646), which is a continuation-in-part of U.S. patent application Ser. No. 14/505,430 filed on Oct. 2, 2014 (now U.S. Pat. No. 9,053,528), which is a continuation-in-part of U.S. patent application Ser. No. 13/542,416 filed on Jul. 5, 2012 (now U.S. Pat. No. 8,855,374), which claims priority to U.S. Patent App. No. 61/504,462 filed on Jul. 5, 2011. Each of these priority applications is incorporated herein by reference in their entirety.

BACKGROUND

The decreased use of pesticides on the one hand and the decreased effectiveness of those which are in use on the other, has resulted in a disturbing proliferation of insects in food and in the home. Moreover, insects and other invading offending objects frequently infest orchards or similar crops, which can cause crop damage and decreased yields. Other types of offending objects can include aircraft such as drones that are used for spying and planning military operations. Some drones have been designed to include firearms that are used to attack targets in military zones. Additionally, offending objects can include undetonated explosives which can cause serious injury and death in post-war zones.

SUMMARY

In one embodiment, described herein is a computer image analysis system, which captures an image of a substrate or other area to be checked for offending objects and is trained to recognize various offending objects commonly associated with such substrates to be checked. If an offending object is identified any of various action operations are taken in different embodiments described herein, including removal of the offending object by way of an action head associated with an imaging device. Another action operation can include destroying the offending object by the action head. In some embodiments, the system is positioned on a movable platform to scan a wide area for offending objects and/or to perform mitigation actions once an offending object is detected.

An illustrative device for use in identifying an explosive includes a processor and an induction heat source in communication with the processor. The induction heat source is configured to emit radiation to heat a metallic component of an explosive device by way of induction. The device also includes a temperature sensor in communication with the processor that is configured to detect heat emitted from the metallic component of the explosive device. The processor is configured to identify a location of the metallic component of the explosive device based on the detected heat. The device further includes an action arm configured to conduct a detonation attempt at the location of the metallic component of the explosive device. A gas sensor of the device is used to detect one or more gases emitted from a non-metallic explosive device.

An illustrative method for detecting explosives includes emitting, by an induction heat source of a detection device, radiation to heat a metallic component of an explosive device by way of induction. The method also includes detecting, by a temperature sensor of the detection device, heat emitted from the metallic component of the explosive device. The method also includes identifying, by a processor in communication with the induction heat source and the temperature sensor, a location of the metallic component of the explosive device based on the detected heat. The method further includes conducting, using an action arm of the detection device, a detonation attempt at the location of the metallic component of the explosive device.

An illustrative device for use in detecting metallic objects includes a processor and an electromagnetic radiation source in communication with the processor. The electromagnetic radiation source is configured to emit radiation to heat a metallic object. The device also includes a temperature sensor in communication with the processor. The temperature sensor is configured to detect heat emitted from the metallic object. The device also includes an alarm configured to notify an operator of the presence of the metallic object responsive to a determination by the processor that a temperature threshold has been exceeded.

An illustrative method for detecting metallic objects includes emitting, by an electromagnetic radiation source of a detection device, radiation to heat a metallic object by way of induction. The method also includes detecting, by a temperature sensor of the detection device, heat emitted from the metallic object. The method also includes determining, by a processor of the detection device, whether the heat emitted from the metallic object exceeds a temperature threshold. The method further includes triggering an alarm responsive to a determination that the temperature threshold is exceeded.

An illustrative mold remediation system includes a processor and an electromagnetic radiation source in communication with the processor. The electromagnetic radiation source is configured to emit radiation to heat a ferromagnetic material in or adjacent to a wall board upon which mold is located. The system also includes a temperature sensor in communication with the processor. The temperature sensor is configured to detect a temperature of the wall board. The processor is configured to compare the temperature of the wall board to a desired temperature to perform mold remediation.

An illustrative method for performing mold remediation includes emitting, by an electromagnetic radiation source, radiation to heat a ferromagnetic material in or adjacent to a wall board upon which mold is located. The method also includes detecting, by a temperature sensor, a temperature of the wall board. The method further includes comparing, by a processor in communication with the electromagnetic radiation source and the temperature sensor, the temperature of the wall board to a desired temperature to perform mold remediation.

Other principal features and advantages of the invention will become apparent to those skilled in the art upon review of the following drawings, the detailed description, and the appended claims.

BRIEF DESCRIPTION OF THE DRAWINGS

Illustrative embodiments will hereafter be described with reference to the accompanying drawings, wherein like numerals denote like elements. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Embodiments of the present subject matter will now be described with reference to the above-identified figures. However, the drawings and the description herein are not intended to limit the scope of the invention. It will be understood that various modifications of the present description are possible without departing from the spirit of the invention. Also, features or operations described herein may be omitted, additional operations or features may be included, and/or features or operations described herein may be combined in a manner different from the specific combinations recited herein without departing from the spirit of the invention.

In one illustrative embodiment, a lens is used to point at a leaf of lettuce and capture an enlarged image thereof via an image capturing device. The image may be stored in digital memory for later analysis or it may be analyzed in real time. In either case, the image is sent to a processor that is trained to recognize the general characteristics and color of the lettuce, and which is also trained to recognize physical characteristics and features of insects typically found on lettuce. The image is magnified so that the presence of the insect, even if well hidden, will be identified by comparison with a library of insects stored in memory. In one embodiment, the processor does not positively identify a bug or other identifiable foreign object, but it may recognize the object as foreign. For instance, a processor may contain parameters of acceptable color values or hues for a specific substrate and if an object is outside of such parameters—software running on the processor determines the object as "foreign."

The identification of the insect can immediately trigger a response in an action head which is attached to the lens housing and is capable of moving to the insect position, and removing or destroying the insect automatically. In another embodiment, rather than removing an observed insect—an action head grips the piece of lettuce and discards it.

Figure 1:
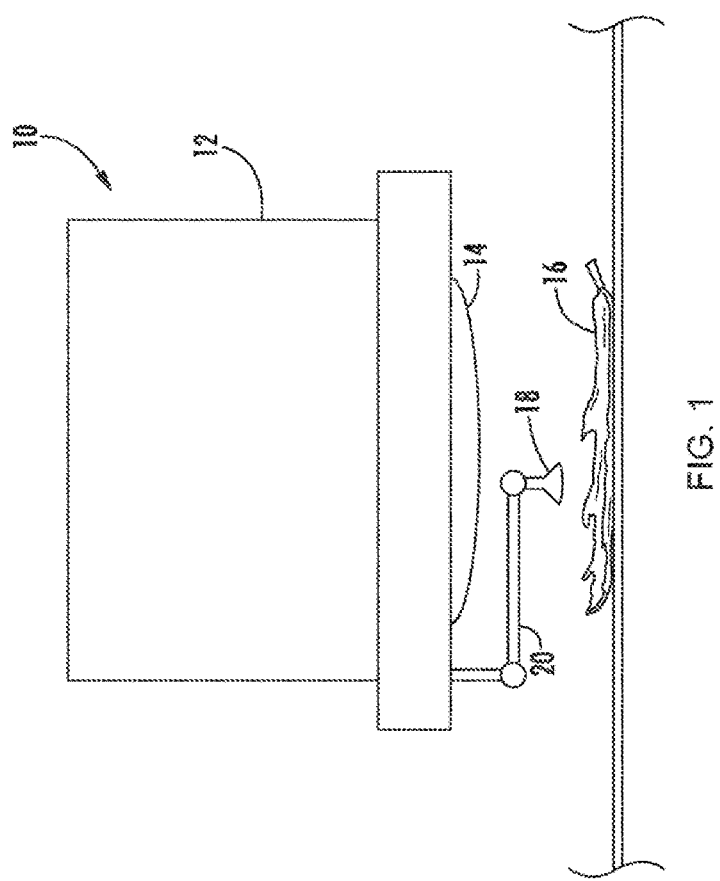
FIG. 1 shows a schematic side view of a scanning device disposed above a substrate to be checked according to an illustrative embodiment.

FIG. 1 shows a scanning device having a casing 12, which houses an image recognition system. A downward facing microscope, lens 14 or any such image capturing device and magnification device is located at a bottom portion of the scanning device. As shown, the lens 14 is directed at a substrate 16, such as, for example, a piece of lettuce. The lens magnifies a segment of a substrate to be checked and it feeds captured images to an image recognition system for image analysis. Images may be stored on a digital storage medium, among other storage systems or media.

It will be understood by those of ordinary skill in the art that the device 10 may be provided with a plurality of differently powered lenses which may be automatically adjusted when greater focusing ability is needed and any of different image capturing devices may be utilized, such as for example, a camera or a video camera, a video telescope, a video monocular, or an array thereof. It should also be understood that the image recognition system need not be housed within the casing 12 of the device—but rather the image recognition software may be provided at a location that is distant from the image-capturing device. In such embodiment, an image-capturing device (e.g. a microscope lens coupled to an image capturing system) is utilized to capture images. The images are then sent by a wired or wireless connection to an image classifier.

FIG. 1 shows an action head 18, which is provided at the distal end of a movable arm 20. The action head may be equipped with one or more instruments, such as a gripping device and/or a suctioning device. In another embodiment described herein, the action head is provided with a heating element or similar heat source—which can destroy a bug or a segment of lettuce when it is brought into direct contact therewith.

In one embodiment, the device 10 housing the lens 14 and action head 18 is a handheld unit, which may be manually or automatically moved across a stationary substrate such as a leaf of lettuce. In another embodiment the device 10 is mounted on a stationary support structure and a conveyor belt positioned below the device delivers items to be scanned below the microscope lens of the device. Still in other embodiments, the device is mounted to a linear motion track and it incrementally moves (for instance by incremental movements of a rack and pinion wheel controlled by a computer) across a substrate to be searched. In one embodiment, the device 10 may be used for purposes of "surveillance." In this embodiment, the device is mounted in a fixed position. When an offending object (such as an insect) enters the field of vision of the lens and is recognized as such by the image recognition system—a command is sent to activate the action head 18 to eliminate and/or neutralize the offending object. It is to be understood that as an alternative to eliminating and/or neutralizing an offending object, the device could mark the offending object for subsequent removal or remedial action. In some embodiments, device 10 may be a drone, which may be a remotely controlled and/or autonomously controlled vehicle (e.g., aircraft, ground vehicle). For example, an autonomous vehicle may be operated according to pre-programmed rules, such as navigation directions (e.g., coordinates or street directions), and/or logical rules to govern operation, such as obstacle avoidance rules and/or task execution rules (e.g., using a scanning or imaging device to assess various subjects).

It should be further understood that the moveable arm described herein may be its own detached unit, but which operates under the control of the software, which software may be stored in memory on the device 10 and configured to run on one or more processors, or which software may be remotely located, such as on a remote server accessible via a data communication signals and/or data networks. An illustrative device control system is described herein with reference to FIG. 4.

In an illustrative embodiment, action head 18 is mounted on an exterior surface of a device such as a drone, a vehicle, or the like. In other embodiments, action head 18 is attached to the distal end of a movable arm. It will be understood that a movable arm may be any of various structures such as, for example, one or more linear guide tracks, rack and pinion systems or such similar relative motion mechanism for supporting and moving an action head. The arm is movable in any of various directions by way of ball joints, linear motion tracks or other such similar movement systems. When a bug or other offending object is detected by the image recognition system, the software is programmed to send a signal to the moveable arm. The moveable arm is then controlled by a software application and directed to the located bug. The action head is deployed to either destroy the bug as described above or to suction it off of the substrate. In one embodiment, rather than directing the action head to a specific location—the moveable arm is directed to push the piece of lettuce (or other substrate) away, thereby discarding the same or removing it from a batch.

The computer used to control operations, execute routines and store data may include at least one or more processors and memory storage devices. The computer also may receive a number of inputs and outputs for communicating information externally.

It is to be understood that the computer which operates the device may operate under the control of an operating system and software applications, components and programs that execute the routines and systems described herein. In general, the routines executed to implement the embodiments, whether implemented as part of an operating system or a specific application, component, program, object, module or sequence of instructions will be referred to herein as "the system", or "software". The software controls the image acquisition, image storage, image analysis and movements of the arm, action head and/or the movement of the device along a track.

It is further to be understood by those of ordinary skill in the art that the described apparatus can include image capturing capabilities and image recognition capabilities coupled with software that is programmed to determine whether or not an object in an image field is an offending object. An "offending object" herein is any physical, identifiable structure or shape that is targeted for action. Examples of offending objects may include, but are not limited to, stationary insects, dirt, mold growth, plant features, product imperfections, drones, flying insects, etc. The device is programmed to take an action once an offending object is detected. "Action" can refer to any remedial steps taken by the device to eliminate or otherwise address the offending object. For example, in one embodiment, the action head 18 of device 10 advances to a location of an offending object and it records the spatial coordinates of the same. The coordinates are stored for later treatment and or elimination.

Figure 2:
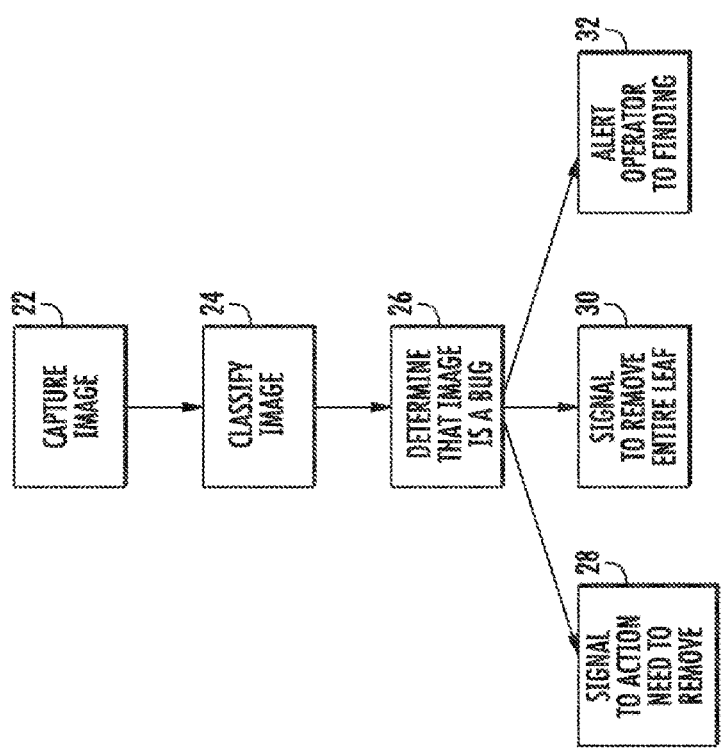
FIG. 2 is a flow chart showing software processing operations according to an illustrative embodiment.

FIG. 2 shows a number of processing steps performed by the software in accordance with an illustrative embodiment. The device is initiated and begins capturing images 22. The images are sent to an image recognition system which classifies various images 24. The classifier may be an algorithmic classifier or a neural network system. The image recognition system is trained to recognize morphological/physical characteristics of bugs or other objects to be detected. The image recognition may also be trained to detect pixel concentrations which may indicate the presence of bug or other objects of interest.

If an image is determined to be a bug 26, then the software performs further processing operations. In one embodiment, the software sends a signal to the moveable arm 28, which directs the action head to the location of the bug to remove the same according to the teachings described above. In another embodiment, the software sends a signal to the moveable arm to push aside the item 30 upon which the bug was detected. Still in another embodiment, upon detecting a bug, the software sends or sounds an alert to a human operator 32. The human operator may intervene to remove the bug or the item.

In another illustrative embodiment, the device can be specifically designed to deal with only one kind of insect on one kind of food or other material, or one other type of offending object. A single kind of action suitable for the situation can be built into such a device.

Extension to a more sophisticated device can be implemented with software taught to deal with many different kinds of foods and materials, to recognize a range of different insects or objects, and different means of removing the insect, including a vacuum, a glue head, an electrical charge, freezing, heat, or even a drop of powerful insecticide. Powerful pesticides sprayed or deposited over a large area are harmful, but a targeted drop on the insect itself will dispatch the insect and not significantly affect the surrounding atmosphere.

In another embodiment, the system can include an array of lenses and response heads so that a sheet being inspected for bed bugs can be continuously passed under the array.

In another embodiment, the system may be used to remove offending objects, such as bugs, from a fluid. In one embodiment, an image capturing device is fixed above a channel of flowing liquid. The device may include an array of image capturing devices or lenses suspended above a channel or similar fluid stream. It will be understood that in one embodiment, the action head may be a vacuum head or suction head such that when the image recognition system detects a presence of an offending object, the software sends a command to the action head to vacuum an area of fluid in the vicinity of the offending object. The vacuum head or suction head can then draw in the offending object, and possibly, some of the surrounding fluid and discard the same.

The present system may be used in any of various environments in which subtle changes need to be detected and then acted on. For example, the beginning of a disease affecting trees or other plants and its subsequent spread is often the result of an insect, beetle or bug penetrating the bark or other surface and destroying the structure from within. Detecting a presence of a specific kind of invader is virtually impossible if it requires a human observer's continued close observation. The instant embodiments can be deployed in a manner which detects and acts whenever an invader is detected on the surface. For example, the software may be trained to detect specific bugs or locusts. Once detected, the software sends a command to spray an offending substance or a pesticide.

In another embodiment, the software is programmed to detect swarms of bugs or other flying objects—irrespective of the type of bugs or objects. In one example, the software is trained to detect a plurality of distinct moving objects within an area of interest. Once a threshold number of moving objects (e.g. >10) is detected, the software will confirm a presence of a swarm and it will automatically send instructions to the action head to address the swarm. In one embodiment, the action head will spray a mist of water vapor or insecticide, smoke laced with insecticide, repellant or similar offending substances. Alternatively, the device can be configured to sound an alarm to disperse the swarm.

The system described herein can be modified to recognize the sign of incipient disease on the skin of a human being at a size that is invisible or almost invisible to the human eye. It is evident that the principles of the proposed systems can be readily applied to other areas where detection, recognition, and action upon a flaw, intrusion, or incipient flaw at a stage where it is barely visible.

Depending on the specific use, the described systems can be associated with a variety of platforms, both mobile and stationary. For example, the image capturing lens and action head may be mounted to a movement mechanism such as a linear guide track, a pulley system, a rack and pinion or any such similar movement mechanisms. Alternatively, the device may be attached to or embedded within a drone, hovercraft, aircraft or similar dirigible. (Mechanical devices/mechanisms for moving the device can be referred to as "movable platforms" herein.) In one in which the device is mounted to a movement mechanism, the software may be programmed to move the device in any of various predetermined or random movements. In such an embodiment, once an offending object is detected, the software sends a command to interrupt movement of the device and deploy the action head to execute one or more remedial actions.

Control of any of the mobile or active platforms envisioned above can be implemented in a variety of ways, including voice recognition. Additionally, the devices and systems described herein, as well as any attendant platform or support, can be supplied with energy in a variety of ways, including batteries, solar, electromagnetic and hard wires, among others.

The proposed systems and devices are not limited to any specific materials of construction or size, and are readily modified by change in programmed recognition patterns to react to different insects, insect parts, plants, plant parts, flying objects, and in some embodiments, to detect extremely small predictable defects or imperfections, among others, in the manufacturing process or in manufactured products. In this latter use, more than one device can be connected to work in tandem, or in any manner called for by the situation.

In one embodiment, the device is furnished with assisted illumination to extend its use at night, through the use of light and infrared, among others. To extend its use further, x-ray and other surface penetrating radiation can be attached to the platform or to the device itself. The image recognition and instant response features of the system can also be incorporated into or provided on the platform.

In one embodiment, a robot platform or movable platform may be provided with an image magnification device to magnify an image of an area, segment and/or substrate to detect objects it is trained to detect.

It is to be understood that in addition to observing and capturing images, the robot or movable platform may be programmed to provide an active response to remove, mitigate and/or react to various conditions. Any of a variety of actions may be deployed by the robot such as, but not limited to, sending an alert or an update, and/or expelling a spray or substance such as pesticide, vapor or smoke. For example, in some embodiments a movable platform such as a robot, vehicle, or drone is utilized to travel about a field, orchard or forest and obtain images of plants and/or trees growing therein. The software detects any of various conditions associated with plants and/or trees and is trained to react accordingly. In one embodiment, the device is trained to detect boring insects (e.g. Emerald Ash Borers) by recognizing physical features such as appearance, color, size, shape etc. Additionally or alternatively, the device detects holes in plants or trees created by such insects. The device then automatically responds by directing the action arm to the detected insect or its entry hole. For example, in one embodiment, the device directs the action arm to an entry hole formed by boring insects and releases a blast of white paint or similar marking material to mark the tree for removal or for remedial treatment.

In a further implementation, the device is programmed to provide an instant response which results in recognition and capture instead of recognition and reject. That is, objects, such as insects, which are of interest instead of being offending, can be trapped and captured with the same device, using only a modification. That is, rather than dispersing or deflecting an object of interest, the software sends a signal to the mechanical arm to capture and maintain the object of interest.

The device may also be deployed for use in quality control activities. In this embodiment, the device may be trained to recognize qualitatively acceptable objects and those that do not meet acceptable criteria (or "defective objects"). The software is programmed to employ an action head to capture defective objects. Acceptable criteria may be any of size criteria, shape criteria or such similar metrics calculated by the software or algorithmic classifier. In other embodiments, acceptable criteria may be based on color criteria, pixel counts, pixel saturation or any such similar image criteria the software and image recognition/analysis software is programmed to analyze.

The devices and systems described herein can also be used as a stand-alone, hand held devices, or devices that are fixed in place with items to be inspected passing through. In one embodiment, the lens/image capture device and action heads can be in a circular or other convenient pattern, and on both sides of the material, as on both sides of a sheet.

In one embodiment, the proposed device is attached to a drone which is programmed to move up and down, and all around a tree periodically, and subsequently to move on to other trees. This will enable the device to protect forests, orchards, and plantations against invasive species. Drones can be programmed to travel in certain sectors of a forest or orchard, around a periphery or in any pattern as designated by an operator to capture images in the area below it and instantly react.

A drone can also be programmed to remain stationary, detecting and protecting against the arrival of an expected invasive species for which it has been trained. Similarly, attaching the device to a robot enables the protection against land based invasive species in addition to airborne species.

In each case, the proliferation of robots and drones, as well as other platforms, extends the use and effectiveness of the device. Included in such other platforms are hovercrafts, extendable legs and floatable devices among others known to those skilled in the art.

Figure 3:
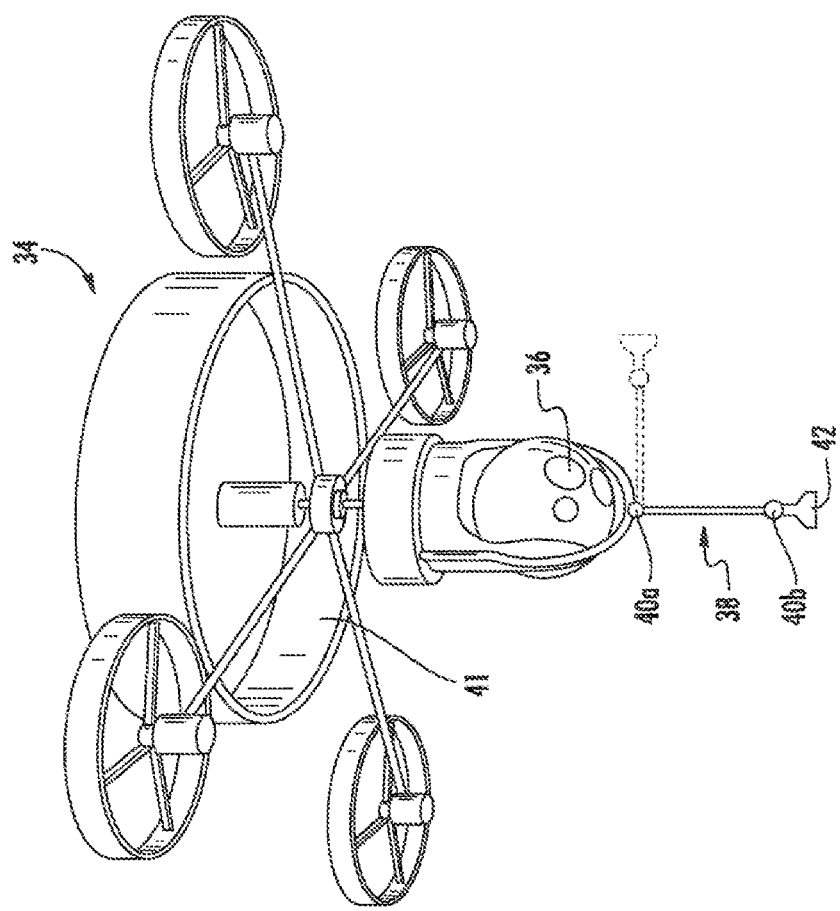
FIG. 3 shows a side perspective view of a scanning device incorporated with a drone according to an illustrative embodiment.

FIG. 3 shows a drone 34 used to capture images and provide an active response according to an illustrative embodiment. Drone 34 has an image capturing device for capturing images of areas to be analyzed. For example, as shown, drone 34 has a lens 36 which is part of a camera or video camera. In one embodiment, the image capturing device is housed in a movable and/or rotatable housing. The lens 36 captures images, which are then analyzed by the image analysis software. The image analysis software may be located in a computer residing in the drone 34 or images may be sent via wire or wireless communication to a computer at another location.

An action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body 41 of the drone, but it could be rotated around joint 40a to a 90.degree. angle.

An action head 42 is shown positioned at the terminal end of action arm 38. The software is configured to direct action head 42 in the direction of a detected offending object and to automatically initiate remedial actions. For example, action head 42 is activated to expel any of various substances described above in response to a command from the software. A tank or similar storage reservoir within the drone stores substances to be dispersed or dispensed from the drone.

In another embodiment, drone 34 is used to capture images of plants or features of plants and to disperse pollen in response to such detection. In some embodiments, the system detects images of plants such as flowers and trees to determine whether or not the plant is a flowering plant adapted for receiving pollen. Additionally or alternatively, the system detects plant objects or features that are adapted to receiving pollen. Upon detection of such plants and/or upon the detection of reproductive features of flowering plants—the drone automatically dispenses pollen. In one embodiment, the pollen is directed to the approximate location of detected flowering plants, but in other embodiments, the pollen is directed to an area proximate to a detected flower or reproductive feature.

In an illustrative embodiment, an image capturing mechanism is used to capture images of plants, trees or other vegetation and image analysis software is utilized to detect objects consistent with flowering plants. As will be understood by those of ordinary skill in the art, the image analysis software may be located in a computer residing in the drone 34 or images may be sent via wire or wireless communication to a computer at a remote location. The image analysis software determines whether or not a plant is one that is adapted to receive pollen and/or whether or not a plant feature is an organ that is adapted to receive pollen (such as a pistil).

In some embodiments, the drone 34 may be directly controlled by a human operator, whereas, in other embodiments the drone is controlled by one or more computers. The drone 34 flies over areas of vegetation and its image capturing system scans the terrain below. In some embodiments, as described above, the image analysis system is trained to detect specific plants for purposes of pollination. In other embodiments, the image analysis system is additionally or alternatively trained to detect specific plant features that are adapted for receiving pollen.

In another illustrative embodiment, once a particular plant-type is detected, the system is programmed to release pollen in the vicinity of such detected plants. That is, once a plant of interest is detected, the software sends a command to the drone to navigate toward such plants and to release pollen.

In other embodiments, the system is programmed to detect specific plant features, like pistils. Once a pistil is detected, the program sends a command to an action arm to release pollen in the direction of the detected pistil. Action arm 38 is shown extending from the body of the drone 34. Action arm 38 has one or more rotatable joints 40a, 40b, ball joints or similar pivoting members allowing for various movement of the action arm 38. For example, in the embodiment shown, action arm 38 is shown pointing downward in an orientation substantially orthogonal to the body of the drone, but it could be incrementally rotated around joint 40a to a 90 degree angle in order to more accurately point the action head 42 in the direction of a pistil.

Action head 42, shown positioned at the terminal end of action arm 38, is provided with a nozzle or such similar spout for releasing a cloud, mist or similar stream of pollen. The software is configured to direct action head 42 in the direction of a flower to be pollinated and automatically expel pollen in the direction of the plant of interest, flower of interest, or plant feature of interest. A tank or similar reservoir within the drone stores substances to be dispersed or dispensed from the drone.

In one illustrative implementation, the system is programmed to detect features associated with almond trees. In this embodiment, once the software confirms a presence of an almond tree, it will automatically send instructions to navigate the drone 34 to an area proximate to the almond tree and subsequently send instructions to the action head 42 to release pollen. In one embodiment, the software is trained to identify flowers on almond trees and to disperse pollen on or near respective flowers. In other embodiments, the system is trained to detect respective reproductive features on flowers of the almond tree (such as pistils) and the action arm is instructed to direct the action head 42 toward the reproductive features. Once the action head is properly oriented, a command is sent to expel a spray or mist of pollen.

In another illustrative embodiment, the software is trained to recognize a specific pistil and initiate a dispersal of pollen that is specific to the pistil of interest. In another embodiment, reservoirs of different pollen types are provided on the drone or similar movable device. The software is trained to recognize and detect a variety of different flowers/pistils (associated with different flowers or flower types) and disperse a pollen type that corresponds to the detected pistil.

It will be understood by those of ordinary skill in the art that drone 34 or a similar aircraft, hovercraft or dirigible having an image capturing device in communication with an image recognition system may be used to detect and monitor any of various conditions and instantly react by dispersing any of various substances or performing other actions via an associated action head. For example, a device may be programmed to detect plant conditions or soil conditions (e.g. using color properties thereof) and to automatically disperse water or nutrients to the detected areas when a dry soil condition or an unhealthy plant condition is detected. In other embodiments, a device may be programmed to detect fires. For example, a drone may be programmed to fly over a forested area and detect visual indicia of smoke or fire. Additionally or alternatively, the device may have a heat sensor to detect fires. Once a fire is detected, the device is programmed to navigate into proximity of the fire and automatically disperse fire retardants such as chemicals or water.

In an illustrative embodiment, the computer which operates the device may operate under the control of an operating system and software applications, components, and programs that execute the routines and systems described herein. In general, the routines executed to implement the embodiments, whether implemented as part of an operating system or a specific application, component, program, object, module or sequence of instructions will be referred to herein as "the system", or "software". The software can control the image acquisition, image storage, image analysis and movements of the arm, action head and/or the movement of the device along a track or other movement mechanism.

Figure 4:
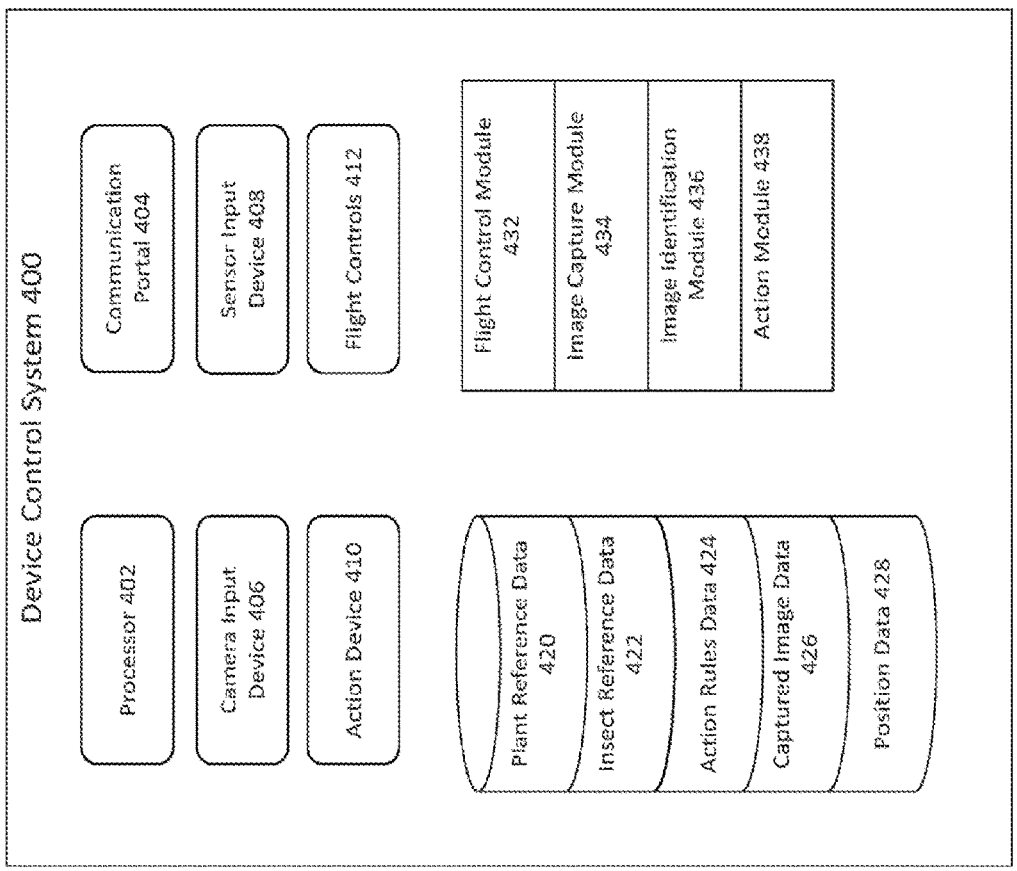
FIG. 4 is a schematic diagram of a device control system according to an illustrative embodiment.

FIG. 4 is a schematic diagram of a device control system 400 in accordance with an illustrative embodiment. The device control system may include a computer system having one or more computers. The device control system may govern operation of an imaging and/or image evaluation device, as may be employed by an imaging drone as described herein. In some embodiments, certain components of the device control system 400 may be located on-board the device, such as on or within a drone, or remotely, such as at a remote computer system, which may be accessible via a data network. For example, the image identification module 436 and/or action module 438 may be located remotely, e.g., on one or more servers. Image data may be uploaded (via physical connection of memory storage devices and/or wirelessly) to the image identification module 436 for evaluation. In some embodiments, action instructions may be transmitted by an action module 438 to one or more drones for execution.

The device control system 400 may include hardware, such as one or more processors 402, a communication portal 404, one or more camera input devices 406, one or more sensor input devices 408 (e.g., scanners, range finders, position sensors (e.g., GPS receivers, altitude sensors, to name a few)), action device 410 (e.g., action head and/or movable arm, as described herein), and/or flight controls 412. Flight controls 412 can include thrusters, engines, motors, turbines, fans, rotors, propellers, thrust vectoring control surfaces, aerodynamic control surfaces, and/or actuators and/or servo motors to move such hardware components. In some embodiments, a drone can include wheels, treads and tracks, or other ground propulsion systems, including motors. In other embodiments, the drone can be designed to float and thus may include floatation devices (e.g., pontoons) or buoyant exterior components of the drone, as well as a water propulsion system.

The device control system 400 may further include non-transitory computer-readable memory (e.g., local and/or remote), which may store and/or access data, e.g., in one or more databases. Such data can include plant reference data 420, insect reference data 422, action rules data 424, captured image data 426 or other sensor data, and/or position data 428, as described herein. The device control system 400 may also include one or more software modules stored in the memory and configured to execute machine-readable instructions to perform one or more processes. Such modules can include a flight control module 432, image capture module 434, image identification module 436, and/or action module 438. The processes and functions described with respect to each module may be performed by one or more other modules, such as other modules described herein or additional modules.

The communications portal 404 may handle, process, support, and/or perform wired and/or wireless communications, such as transmitting and/or receiving data (e.g., data packets). In embodiments, transmission described with respect to a single data packet may comprise a plurality of data packets. Data packets may be discrete electronic units of data. In other embodiments, transmissions may comprise non-discrete signals, such as data streams. Transmissions described with respect to data packets may also comprise data transmissions via other communications mechanisms known in the art, such as data streams. Communications portal 404 can comprise hardware (e.g., hardware for wired and/or wireless connections, such as communications chipsets, communications interfaces, and/or communications antennas, to name a few) and/or software.

Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Wired connections may be provided through telephone ports, Ethernet ports, USB ports, and/or other data ports, such as Apple 30-pin connector ports or Apple Lightning connector ports, to name a few.

Wireless connections may include cellular or cellular data connections and protocols (e.g., digital cellular, PCS, CDPD, GPRS, EDGE, CDMA2000, 1.times.RTT, Ev-DO, HSPA, UMTS, 3G, 4G, 5G, and/or LTE, to name a few), Bluetooth, Bluetooth Low Energy, Wi-Fi, radio, satellite, infrared connections, ZigBee communication protocols, to name a few. Communications interface hardware and/or software, which may be used to communicate over wired and/or wireless connections, may comprise Ethernet interfaces (e.g., supporting a TCP/IP stack), X.25 interfaces, T1 interfaces, and/or antennas, to name a few.

Turning to the data that the device control system 400 may store and/or access, plant reference data 420 can include one or more images of each of a plurality of species for image comparison purposes and/or an identifier or database association to indicate the respective species associated with each image. In embodiments, the plant reference data can include images of plant parts, such as a pistil, petal, or leaf, to name a few. Plant reference data can also include growing condition data, which may be coupled with GPS data of captured images to narrow the number of reference images that are likely to produce a match. Growing condition data can include any of water availability, soil type, temperature information (e.g., temperature ranges), climate, geographic location information, etc.

Insect reference data 422 can include one or more images of insects of various species or insect components (e.g., wings) and an indicator or reference to associate each image with its respective species. Insect reference data may include size information (e.g., cross-sectional measurements, measurements of body components, such as body segments, antennas, legs), body information (e.g., number of body segments, number of antenna), color information, geographic information (e.g., indicating where the insect is likely to be found), habitat information (e.g., indicating habitats in which the insect is likely to be found, such as they type of crops, type of terrain, temperatures), and/or food source information.

Action rules data 424 can comprise rules to control an action device 410 (e.g., to control movement and/or usage of the action device 410) and/or logical rules to govern when to use the action device 410.

Captured image data 426 can comprise one or more images (e.g., image files), sequences of images, and/or videos (e.g., video files). Captured image data 426 may be associated with position data indicating a position of the subject of the image and/or a position of the drone or camera. The device control system 400 may further store and/or access additional sensor data from other sensor input devices 408, such as range information (e.g., from the drone or camera to an image subject), infrared imaging data, heat imaging data, temperature information, and/or ambient light intensity information, to name a few.

Position data 428 can include global positioning coordinates (e.g., indicating latitude, longitude, and/or altitude or elevation), street address information, and/or local coordinate information (e.g., one, two or three-dimensional locations in relation to the drone or camera).

A flight control module 432 may control movement of a drone, such as by controlling thrust, control surfaces or other flight control hardware 412.

An image capture module 434 may govern when and how to capture images (e.g., which subject to focus on, zoom level, type of imagery to capture (still versus video), and/or number of images to capture, etc.).

An image identification module 436 or image classifier may perform image analysis, such as comparisons to reference images and/or reference data as described herein, to detect one or more subjects in a captured image, such as plant species, insect species, insect quantities, and/or other foreign objects.

An action module 438 may evaluate action logical rules with respect to captured and processed image data to determine one or more actions to take. The action module may also control one or more action devices (e.g., such as an action head and/or movable arm attached thereto) to cause them to carry out the determined actions.

Figure 5:
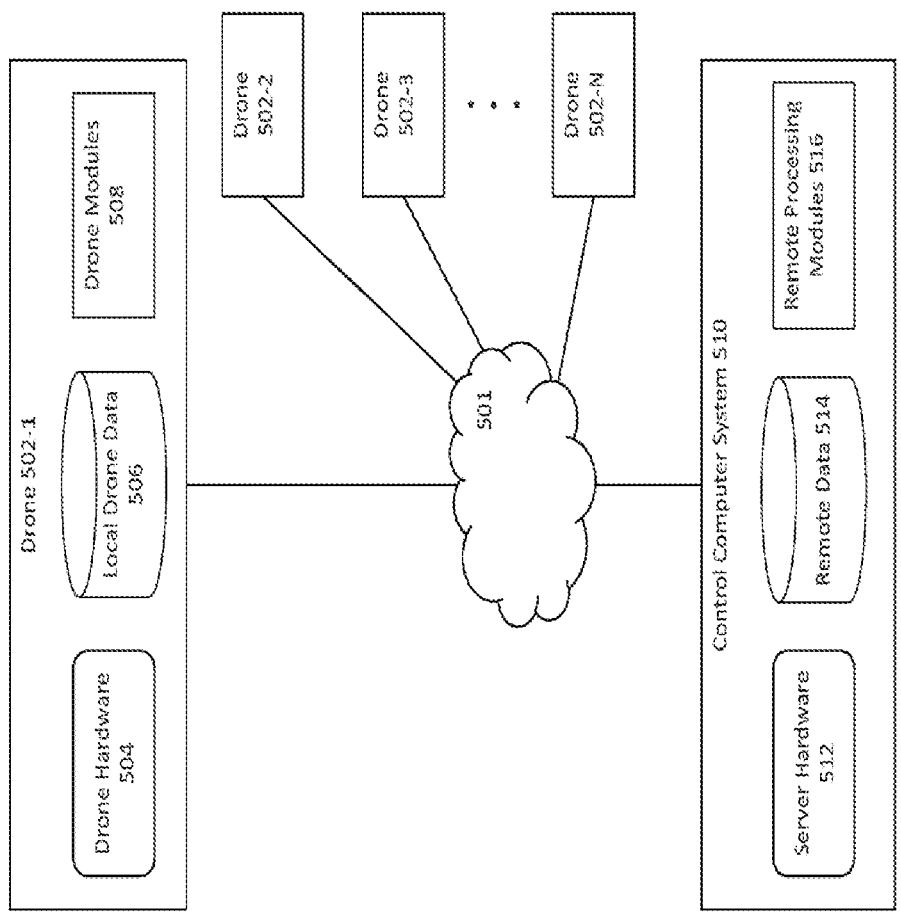
FIG. 5 is a schematic diagram of a drone scanning system according to an illustrative embodiment.

FIG. 5 shows a schematic diagram of a drone scanning system in accordance with an illustrative embodiment. The system can comprise one or more drones 502 (e.g., drones 502-1, 502-2, . . . 502-N) and/or a control computer system 510, which may be remotely located, such as on one or more servers. The devices (e.g., drones) and/or computer systems may be operatively connected directly, e.g., via wired or wireless communications, and/or indirectly, e.g., via a data network 501, such as the Internet, a telephone network, a mobile broadband network (e.g., a cellular data network), a mesh network, a local area network (LAN) (including a wireless local area network, e.g., a Wi-Fi network), a wide area network (WAN), a metropolitan area network (MAN), and/or a global area network (GAN), to name a few. Data networks may be provided via wired and/or wireless connections. Data networks may be public or private. Accordingly, data networks may be open or closed, such as requiring authorized access, specific communication connections, or specialized hardware and/or software. In some embodiments, any combination of communications channels may be utilized.

Processing of data from one or more drones 502 and/or control of each drone may be performed by one or more respective processors contained within or on each drone, one or more processors contained within or on one or more master drones that transmit commands to subordinate drones, and/or performed remotely such as at a remotely located control computer system, which may be one or more servers comprising one or more computers that receive data from and/or transmit instructions to the drones. In embodiments, any of the data processing and/or device control functions may be divided among entities, such as the drones 502 and remote control computer system 510. For example, flight controls or vehicle movement may be handled at each device, while image processing may be performed remotely. In embodiments, data acquisition may be handled at the device (e.g., capture of images and/or sensor data) and transmitted to the remotely located control computer system 510. The computer system 510 may process such data as described herein (e.g., perform image recognition and/or determine actions), and/or transmit instructions (e.g., action instructions, which may be machine-readable instructions to execute one or more determined actions) to the device 502 or to one or more other devices. Accordingly, one or more first drones 502 may acquire data while one or more second drones 502 may execute actions based upon determinations from the acquired data.

Both drones 502 and the control computer system 510 may include one or more processors, memory devices storing data in non-transitory computer-readable memory, which data may be organized in one or more databases, and communication portals (e.g., communications antennas and/or chipsets, as described herein). Drones and the control computer system may further comprise one or more input devices, e.g., to receive direct user input. Accordingly, drones may have keypads, touch screens, buttons with hardwired or programmed functionality, microphones, cameras (e.g., with gesture processing software), or other input devices. The control computer system 510 may include one or more input devices such as keyboards, mice, touchpads, touchscreens, microphones, cameras, etc., and/or output devices (e.g., display screens or speakers, etc.).

Each drone 502 may also include the respective hardware 504 (e.g., cameras, sensors, vehicle propulsion and control hardware), data 506 (e.g., rules for autonomous movement or control, flight path data, reference imagery and/or data, and/or captured data), and software modules 508 (e.g., any of the software modules described with respect to FIG. 4) to operate in such a divided control system.

Similarly, the control computer system 510 can include the hardware 512 (e.g., processors, memory devices, and/or communication portals), data 514, and/or software modules 516 running on one or more processors to perform its assigned functions. Accordingly, remote data 514 can include databases of reference imagery and/or other reference data, which may be used in image analysis. Remote data 514 can also include a repository of captured images and/or other sensor data, such as from across time periods and/or from a plurality of drones.

Remote processing modules 516 may include flight control modules, e.g., for controlling navigation routes or destinations, image analysis modules, and/or action modules to determine actions to take. The remote control computer system 510 may receive data from one or more drones, store such data, process such data, and/or generate and transmit machine-readable instructions to the drones.

As discussed above, in one embodiment, the device is an apparatus having image capturing capabilities and image recognition capabilities coupled with software that is programmed to determine whether or not an object in an image field is a pistil. A "pistil" herein is any physical, identifiable structure or shape of a plant part that is adapted to receive pollen. Once a pistil is detected, an automatic response in an action arm directs pollen to the identified pistil.

As also discussed above, the device set forth herein may be programmed to provide an active response to remove, mitigate and/or react to various biological conditions. For example, in some embodiments, the device may be programmed to detect a presence of skin conditions and send an alert or expel a marking material to a body site where a condition is identified. In an illustrative embodiment, the device is programmed to detect ticks embedded on user's skin by recognizing physical features consistent with ticks, such as appearance, color, size, shape etc.

The tick-detecting device may be disposed on a movable platform, for example, as set forth herein, and programmed to move across an external aspect of a person or of a limb. In other embodiments, the device is a handheld unit that is grasped and manipulated by a user.

When a tick, bite, or mark is identified, the device automatically responds by directing the action head to the location of the detected tick and releases a blast of degradable ink, paint or similar marking material to designate a need for careful inspection or removal as the case may be.

In some embodiments of the invention, the device is programmable to be tailored to identified users for more specific tick detection. In such embodiments, the device is initially deployed to image the entire skin surface of a given user. The device detects all images that contrast with normal skin tone, and stores each of the images in a database (e.g. on a digital storage medium). Thus, after initial deployment, the system's database will have images of each mole, scar, or other dark marks on the user's skin. Upon subsequent deployment, the system will search for contrasting images and compare each contrasting image detected against the stored database. If a match is found, then the system can determine that the detected image was previously present on the user and no action is necessary. If, however, an image is detected for which there is no match—the system will then direct the action head to mark the newly found image. In this embodiment, a tick will present as an image for which there is no corresponding match, and it will trigger a response of the action head as set forth above.

Still in other embodiments, the device set forth herein may be programmed to provide an active response to remove, mitigate and/or react to various agricultural conditions.

For example, the device may be deployed in a field, garden, or orchard to detect early indications of weeds or similar harmful plants. The device may be provided on a stationary structure to scan an area of a field. Alternatively, the device may be mounted on a movable platform such as a robot, vehicle, or drone that is utilized to travel about a field and obtain images of plants growing therein. The software is programmed to distinguish between a weed and a desired crop or plant. When it detects any of various features associated with weeds or other undesired vegetation it will automatically react. In one embodiment, the device is trained to detect weeds by recognizing physical features such as appearance, color, size, shape etc. In the event that weeds are detected, the device automatically responds by directing the action arm to the detected weed or plant and releasing herbicide to the vicinity of the detected weeds.

In another illustrative embodiment, the devices and systems described herein can be in the form of a security system used to identify and/or target other offending objects, such as drones and other mechanical devices which can move in the air, on the ground, or through the water. Such security systems can be used to keep an area secure and/or free from threats. For example, such a security system can be used by a prison to prevent drones from flying over prison grounds and delivering contraband to prisoners. Such a security system can also be used to help protect military bases, bunkers, supply caches, communication towers, homes, etc. from spying and/or attacks implemented using mechanical devices.

In one embodiment, a security system can include a mobile platform that allows the system to traverse land, air, and/or water. For example, the system can include tracks that allow the mobile platform to move along the ground, propellers or other thrust component to allow the mobile platform to move through the air, and/or lightweight inflatable pontoons using in conjunction with a thrust component that allows the mobile platform to float and move through the water. The system can also include one or more image capture devices, one or more processors, one or more computer memories, one or more communication components for communicating with remote systems, control and logic software, and/or one or more detectors such as motion detectors, sound detectors, wireless signal detectors, one or more action arms, etc. mounted to the mobile platform.

The one or more image capture devices for the security system can include still cameras, video cameras, infrared imaging devices, x-ray imaging devices, magnification lenses, etc. that are configured to capture images of a given area. Captured images/data can be stored in a computer memory of the security system and/or transmitted to a remote storage/processing system using the communication components. The computer memory of the security system can also be used to store the control and logic software, which can be used to identify objects and make determinations regarding what, if any, action is to be taken upon identification of an object. The logic can include image recognition software that can be used to analyze images/video captured by the system to determine if any offending objects are present. The control and logic software can be executed by the one or more processors of the system. In an illustrative embodiment, the security system can be configured to determine whether an identified object is a living object (i.e., person, bird, animal, etc.) or an inanimate object (drone, robot, etc.). The action taken by the system can be based in part on whether the object is living or inanimate.

The one or more sensors of the security system are used to detect the presence of objects and to help determine whether detected objects are considered offending objects. A motion detector sensor can be used to identify motion, which can be indicative of an approaching object. A microphone or other noise detector can be used to detect sounds which can be indicative of an approaching object, such as motor noise, propeller noise, electronics noise, voices, etc. A wireless signal detector can be used to detect approaching objects based on wireless signal transmissions made by the approaching object. The security system can also include a temperature probe detector for determining the temperature at or near an approaching object. The security system can also include an infrared detector to detect whether an approaching object is releasing any heat.

Figure 6:
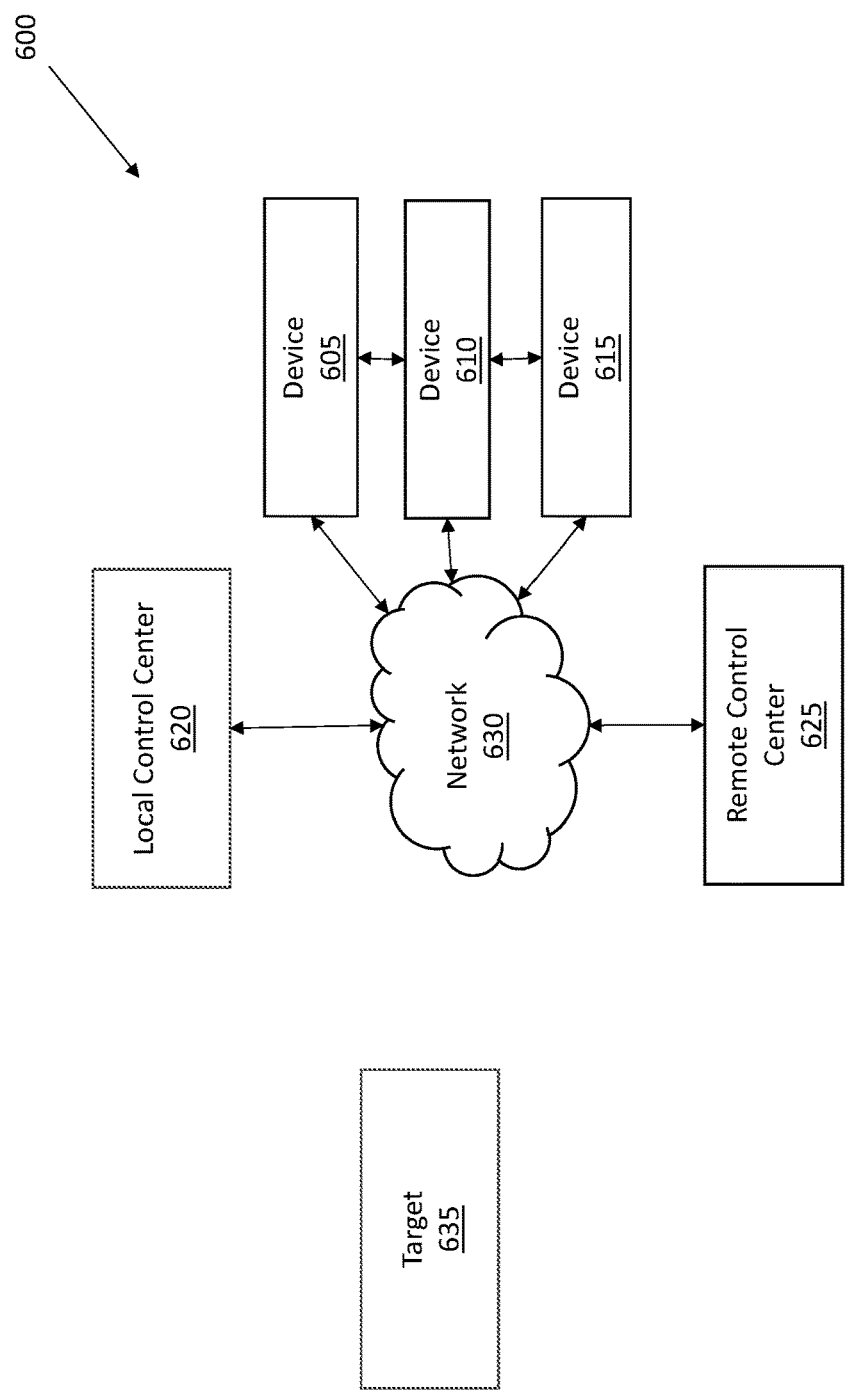
FIG. 6 is a block diagram depicting a system to target mechanical offending objects in accordance with an illustrative embodiment.

FIG. 6 is a block diagram depicting a system 600 to target mechanical offending objects in accordance with an illustrative embodiment. As depicted, the system 600 includes a device 605, a device 610, a device 615, a local control center 620, a remote control center 625, and a network 630. In alternative embodiments, the system 600 can include fewer, additional, and/or different components. In an illustrative embodiment, each of the devices 605, 610, and 615 can be mechanical devices which are configured to monitor an area and take action based on the monitoring. The area being monitored can be a school, a prison, a government building, a home, a business, a warehouse, a military base, etc.

In an illustrative embodiment, each of the devices 605, 610, and 615 can include a mobile platform, an image capture device, one or more sensors, a processor, a memory, a transceiver, a power source, and an action arm. The mobile platform can allow the devices 605, 610, and 615 to fly through the air, to move along the ground, and/or to float and move on water. As such, each of the devices 605, 610, and 615 can be in the form of a drone, watercraft, wheeled vehicle, robot, etc. The one or more sensors on the devices can include motion detector sensors, microphones, temperature sensors, wireless signal sensors, infrared sensors, etc. As discussed above, these sensors can be used to detect the presence of an object and/or to determine whether a detected object is living or inanimate.

The memory of the devices 605, 610, and 615 can be used to store algorithms and operating logic, and the processor can execute the algorithms and logic. The transceiver, which can be controlled by the processor, allows the devices 605, 610, and 615 to communicate with one another, either directly or through a network 630. The transceiver also allows the devices 605, 610, and 615 to communication with the local control center 620 and the remote control center 625. The network 630 can be any type of network known in the art, such as a cellular network, a short-range communication network, a radio frequency network, the Internet, etc.

The local control center 620 can be proximate to the area being monitored, and can include docking stations or other components to periodically charge the power sources of the devices 605, 610, and 615. The power sources can be in the form of batteries or any other charge generating/storing devices. The local control center 620 can also include at least a processor, memory, and transceiver. The local control center 620 can be configured to receive images/video captured by the image capture device and data detected by the sensors, and can process that received data to determine whether a possible target, such as a target 635, is present. In the event of a possible target, the local control center 620 can generate instructions for one or more of the devices 605, 610, and 615 to take action. In an alternative embodiment, each of the devices 605 may perform data processing on-board and may make independent decisions regarding any action to be taken.

In another embodiment, any of the processing and/or decision-making can be performed by the remote control center 625. The remote control center 625 can be located in a remote position relative to the area being monitored by the system. As one example, the remote control center 625 can be a hub/facility which is tasked with the monitoring of a plurality of different locations. In one embodiment, data processing and instruction generation can normally be performed at the local control center 620 or on-board the devices 605, 610, and 615, but can be overridden by the remote control center 625 for sensitive or particularly important scenarios. In an alternative embodiment, the remote control center 625 may not be included.

In an illustrative embodiment, one or more of the devices 605, 610, and 615 can identify the target 635 using its image capture device and/or other sensors. The target 635 can be a drone or other mechanical device, a person, or an animal. Upon detection of an object, the system determines what, if any, action is to be performed by the devices 605, 610, and 610. In one embodiment, the system 600 determines whether the target 635 is living or inanimate and bases the action determination on the result. For example, if the target 635 is determined to be living, the system 600 may perform one or more notification operations to alert appropriate individuals of a person or other living thing the area that is being monitored. If the target 635 is determined to be inanimate, the system 600 can instruct one or more of the devices 605, 610, and 615 to take action using their action arms.

In one embodiment, if a determination is made by the system 600 to take action, one or more of the devices 605, 610, and 615 is instructed to use their action arms to capture or disable the target 635. The target 635 can be captured by a net that is launched from an action arm of one of the devices, and that is configured to inhibit further movement of the target 635. The action arm can also be used to fire a projectile at the target 635 to disable it. The projectile can be a bullet, a rubber bullet, a bean bag, a paint ball, an arrow, or any other type of projectile. In one embodiment, the action arm can include a flamethrower that is configured to direct fire toward the target 635. The action arm can also include a laser that is configured to direct a laser beam at the target 635 to disable or destroy it. The action arm can further include a signal jammer or interference unit that is designed to disable wireless communications from being transmitted or received by the target 635.

In another illustrative embodiment, any of the systems described herein can be used for detection of explosive devices such as landmines, bombs, artillery, etc. Thousands of individuals die every year as a result of unintentional detonation of explosive devices such as abandoned landmines. A landmine refers to a type of explosive device that is positioned on the ground or just under the surface of the ground as part of a military operation. The landmine is designed to explode when contacted or approached by an individual or vehicle. Thousands of landmines may be placed during a military conflict. Unfortunately, the landmines are often not removed at the conclusion of the conflict, which creates a very dangerous environment for animals and individuals living in the area. Other unexploded munitions such as bombs, artillery shells, missiles, etc. can also cause hazardous conditions.

Described herein is a system that is configured to detect and act upon undetonated explosives. In one embodiment, the system can use the principle of induction heating to identify explosives above, at, and below ground level. The system can also be configured to use gas sensing to identify the explosive devices. Specifically, one or more gas sensors are used to identify the presence of gases which are released over time as certain types of explosive devices degrade. The system is also configured to take an action with respect to the identified explosive such as cause detonation, mark the location, transmit data regarding the location, etc.

Figure 7:
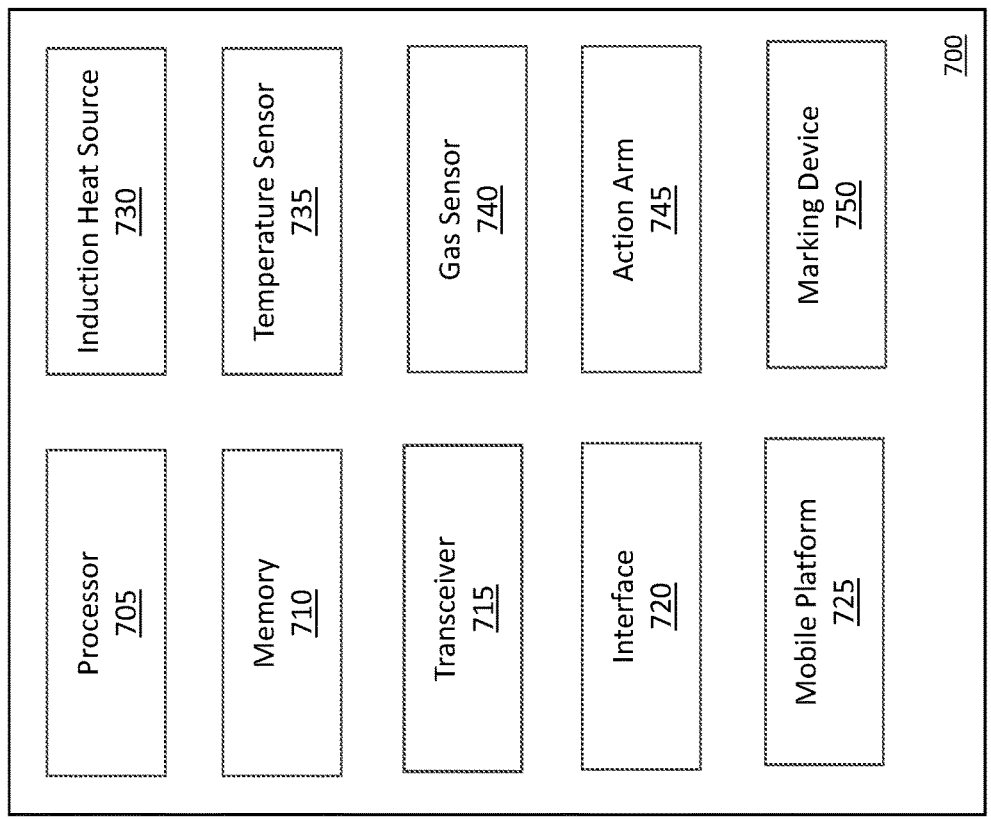
FIG. 7 is a block diagram of a system to target undetonated explosive devices in accordance with an illustrative embodiment.

FIG. 7 is a block diagram of a system 700 to target undetonated explosive devices in accordance with an illustrative embodiment. The system 700 includes a processor 705, a memory 710, a transceiver 715, an interface 720, a mobile platform 725, an induction heat source 730, a temperature sensor 735, a gas sensor 740, an action arm 745, and a marking device 750. In alternative embodiments, the system 700 may include additional, fewer, and/or different components. For example, the system 700 may include a power source, a protective housing, a camera, and/or any of the other functionality and hardware described herein for the various systems.

The processor 705 of the system 700 can be any type of computer processor or controller known in the art. Similarly, the memory 710 can be any type of computer memory or storage known in the art. The memory 710 can be used to store operating instructions for the system 700, algorithms for identifying explosive devices, algorithms for taking action with respect to identified explosive devices, communication algorithms, navigation algorithms, etc. The processor 705 can be in communication with the memory 710 and configured to execute any of the operating instructions and algorithms stored in the memory. The processor 705 can also be used to interact with and control any of the other components of the system 700.

The transceiver 715 can be any type of transmitter and/or receiver known in the art. The transceiver 715 allows the system 700 to communicate with a remote location such as a docking station, a control station, a handheld remote control unit, cellular towers, satellites, etc. The transceiver 715 allows the system 700 to receive remote instructions and/or to provide captured data to a remote location. For example, as discussed in more detail below, the system 700 can be used to identify an explosive device that has not detonated. In one embodiment, upon identification of the explosive device, the system 700 can use the transceiver 715 to transmit an image and/or other data regarding the identified explosive device such that a remote user can instruct the system 700 with an appropriate course of action. In an alternative embodiment, the system 700 can include instructions in the memory 710 that instruct the system 700 on how to respond to one or more types of different identified explosives.

The interface 720 can include any components that allow a user to interact with the system 700. The interface 720 can include a display, a keyboard or keypad, one or more ports, etc. The user can utilize the interface 720 to exchange information with the system 700, to program the system 700, to conduct diagnostics on the system, etc. In an alternative embodiment, the interface 720 may not be included in the system 700.

The mobile platform 725 can include one or more housings used to mount the components of the system 700. The mobile platform 725 also allows the system 700 to traverse land, air, and/or water. For example, the mobile platform 725 can include tracks and/or tires that allow the mobile platform to move along the ground. The mobile platform 725 can also include one more propellers, blades, or other thrust component to allow the mobile platform to move through the air. For example, the mobile platform 725 can include any air drone components known in the art. The mobile platform 725 can also include flotation and propulsion components that allow the system to float and move through water. The flotation components can include lightweight inflatable pontoons or other buoyant material, and the propulsion component can include a propeller or jet.

The induction heat source 730 of the system 700 can be used to generate detectable heat in a metal component that forms an explosive device (e.g., a housing of the explosive). The induction heat source 730 can include an electromagnet and an electromagnetic radiation source that can be in the form of an electronic oscillator that passes a high frequency alternating current through the electromagnet. Alternatively, the induction heat source 730 can include any other electromagnetic radiation source that can be used to induce heat in a metallic object. The radiation emitted by the induction heat source 730 can be targeted such that it causes eddy currents to form in a metallic object such as an explosive housing, which in turn causes the metallic object to heat up. If the metallic object is ferromagnetic, heat may also be induced via magnetic hysteresis losses as known in the art.

The temperature sensor 735 can be any type of temperature probe, thermometer, thermocouple, etc. known in the art for detecting heat. In an illustrative embodiment, the temperature sensor 735 is used to detect a metallic object by detecting heat that emanates from the metallic object as a result of exposure to radiation from the induction heat source 730. In one embodiment, the temperature sensor 735 can be on a movable arm or other component that allows for precise positioning of the temperature sensor 735 such that the temperature sensor 735 can be placed into an area of interest (e.g., near the ground or in the ground) to detect heat. Upon detection of heat, the system 700 can determine that there is a potential explosive in the area. In an illustrative embodiment, the temperature sensor 735 detects the heat as a differential between ambient environment conditions and the heat emitted from the metallic object as a result of the induction heating.

The gas sensor 740 can be used to detect one or more gasses that are commonly emitted from an explosive over time. For example, it is known that many explosive devices emit detectable chemical vapor(s) such as nitrogen dioxide, 2,4,6 trinitrotoluene, 2,4 dinitrotoluene, 1, 3 dinitrobenzene, etc. As with the temperature sensor 735, the gas sensor 740 can also be on a movable arm or other component that allows for precise positioning of the gas sensor 740 relative to a surface of interest such as the ground or under the ground. In one embodiment, the gas sensor 740 can be used independent of the induction heat source 730 to detect explosive devices that do not contain metal and which therefore cannot be heated via induction (i.e., plastic explosives). In an alternative embodiment, the gas sensor 740 can be used in conjunction with the induction heat source 730. For example, upon detection of a metallic object using the induction heat source 730 and the temperature sensor 735, the gas sensor 740 can be used to determine if any gas(es) indicative of an explosive device are present in the area to improve the likelihood that the identified metal is actually an explosive device.

In one embodiment, upon detection of a possible explosive device, the system 700 can be configured to take action to attempt to detonate the explosive device. The action arm 745 can include one or more components that can be used to perform the detonation. In one embodiment, the action arm 745 can include a contact surface that is configured to physically contact the explosive (e.g., landmine) to cause detonation in the same way that individual walking over the explosive would cause it to detonate. The action arm 745 can also include components to generate a high thrust blast of air (or other gas) to cause the detonation without physically contacting the explosive. In one embodiment, the action arm 745 can include a compressed gas canister (e.g. carbon dioxide) to generate the high thrust blast. The action arm 745 can also include a gun, slingshot, pressurized launcher, or other component configured to shoot a projectile at the explosive to cause detonation. In an alternative embodiment, the system 700 can use the induction heat source 730 to generate a large amount of heat at the explosive device to cause the detonation.

The marking device 750 can be used to mark the location of a possible explosive device. The marking device 750 can include a paint source to apply a paint to the ground where the explosive may be located. The marking device 750 can also determine, save, and/or transmit coordinates of the possible explosive using a highly accurate electronic positioning system incorporated into the system 700. For example, coordinates can be determined using temporary and/or permanent base stations and triangulation as known in the art. A high accuracy global positioning system (GPS) can also be used alone or in combination with a dead reckoning system to achieve coordinates with accuracy down to the range of inches. Any other electronic positioning system known in the art can also be used.

In one embodiment, the marking device 750 can be used in the event that a possible explosive is found but unable to be detonated by the system 700 after one or more detonation attempts. Alternatively, the marking device 750 can be used to mark any location at which a possible explosive is identified, regardless of whether a detonation attempt is made. In one embodiment, the system 700 can be programmed to make a determination of whether to use the marking device 750 to mark the location of a possible explosive device or the action arm 745 to attempt to detonate the possible explosive device. The determination can be based on the specific location at which the possible explosive device is located (e.g., extra caution may be used in an area close to homes, roads, etc.).

As an example, the system 700 can be used to survey an area to identify and/or dispose of any undetonated explosives. The area can be a prior military zone in which it is known or suspected that landmines and/or other explosives are present. The system 700 can use the mobile platform 725 to either fly over the area or drive over the area to perform detection tests. In one embodiment, the system 700 can use the transceiver 715 to communicate with a remote control station (or remote control unit) to provide information as it is detected and receive instructions responsive to the provided information. The instructions can include performing a detonation attempt, marking a location, and/or conducting additional detection testing of the location to help confirm what is present.

As the system 700 moves over the area, the system can utilize the induction heat source 730 to emit electromagnetic radiation that will induce heat in metallic objects that are proximate to the radiation. The metallic objects can be at, above, or below the ground surface. The temperature sensor 735 can be used in conjunction with the induction heat source 730 to detect heat from the metallic object(s), which is indicative of the presence of metal. In one embodiment, a temperature threshold (e.g., 1 degree above ambient conditions, 3 degrees above ambient conditions, 5 degrees above ambient conditions, etc.) can be used to reduce false positives caused by small pieces of metal and/or minerals. For example, if the detected temperature is less than the temperature threshold, the system 700 can determine that the identified metal is not part of an explosive. In an illustrative embodiment, the temperature sensor 735 is positioned on an arm or other movable component that allows precise positioning of the temperature sensor at a location which is being targeted with radiation by the induction heat source 730. The arm or other movable component also allows the temperature sensor 735 to positioned away from the system 700 such that heat generated by the system 700 does not interfere with the temperature sensor 735.

In one embodiment, upon detection of heat that satisfies the temperature threshold, the system 700 can attempt to detonate an explosive associated with the detected metal. In such an embodiment, the action arm 745 is activated to perform detonation. If the detonation is successful, the system 700 may be sacrificed. However, the cost of replacing the system 700 is negligible compared to the potential loss of human/animal life that could have otherwise resulted had the explosive detonated in response to human/animal contact. In an alternative embodiment or in situations where the detonation attempt fails, the system 700 can use the marking device 750 to mark the location for future action.

In one embodiment, the system can also use the gas sensor 740 to help detect possible explosives. The gas sensor 740 can be used to help confirm that detected metal (i.e., metal detected using the induction heat source 730) is actually associated with an explosive device based on the presence or absence of one or more signature gases associated with the decay of an explosive. Alternatively, the gas sensor 740 can be used independent of the induction heat source 730 and temperature sensor 735 to detect explosives based solely on the presence of the aforementioned gas(es). The action arm 745 can be used to attempt to detonate any explosives used by the gas sensor 740. The marking device 750 can also be used to mark the location in addition to or alternative to the detonation attempt.

The systems described herein can also be used in detector applications, such as portable or stationary metal detectors. In one embodiment, a stationary induction detector system can be positioned at an entrance to a facility/event, and used to determine whether individuals entering a store, park, concert, hotel, airport, etc. are carrying metal. The stationary induction detector system can be implemented as a walkway through which individuals are required to pass prior to gaining entry, similar to metal detection systems used in airports and other buildings. In one implementation, the stationary induction detector system generates electromagnetic radiation that causes an increase in temperature of ferromagnetic metals that are positioned within the stationary induction detector system. Thermal sensors are positioned within the detection system and are used to trigger an alarm if metal is determined to be present.

In another implementation, an induction detector system can be a portable device in the form of a handheld unit such as a wand, etc. The handheld induction detector system can be used by security guards to scan individuals entering a facility/event. Specifically, the handheld induction detector system can generate electromagnetic radiation and use one or more on-board temperature sensors to detect an increase of temperature in present metals that results from the electromagnetic radiation. The portable device can also be used in military operations to identify metallic objects behind walls of buildings or within the walls of buildings. The portable device can also be used by construction crews to identify metal within a wall. For example, the portable device can be used to detect the location of water pipes within walls, electrical wiring within walls, bombs behind walls, firearms behind walls, etc.

Figure 8:
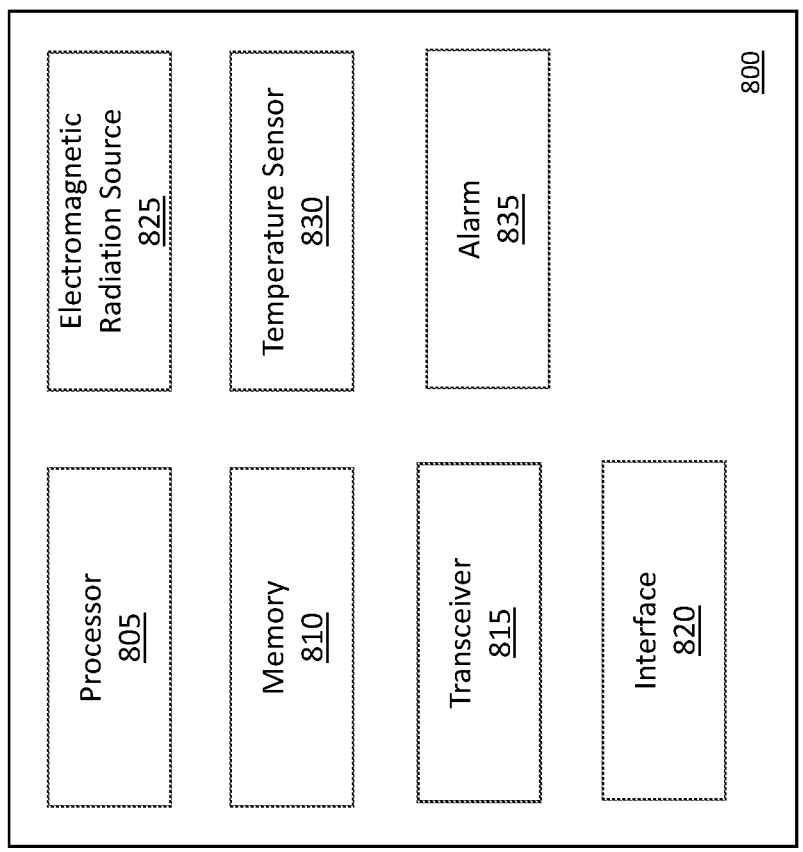
FIG. 8 is a block diagram of an induction detector system in accordance with an illustrative embodiment.

FIG. 8 is a block diagram of an induction detector system 800 in accordance with an illustrative embodiment. The induction detector system includes a processor 805, a memory 810, a transceiver 815, an interface 820, an electromagnetic radiation source 825, a temperature sensor 830, and an alarm 835. In alternative embodiments, the induction detector system 800 may include fewer, additional, and/or different components. As discussed above, the induction detector system can be implemented as a stationary unit or a portable unit, depending on the application.

The electromagnetic radiation source 825 can be any type of electromagnetic radiation generating system known in the art. In the embodiment of a stationary induction detector system, the electromagnetic radiation source 825 directs the electromagnetic radiation to a detection area inside of a gate, tunnel, arch, chamber, etc. in or on which the components of the induction detector system 800 are mounted. For example, individuals being tested by the detection system can be directed to stand on a certain spot/location which forms the detection area. Alternatively, the detection area may be a larger area that is monitored without asking the user to stand on a certain spot/location. As a result of the electromagnetic radiation, any ferromagnetic metal within the detection area heats up. The temperature sensor 830 is used to detect the resulting heat caused by the interaction of the metal and the electromagnetic radiation. The temperature sensor 830 can be any of type of temperature/thermal sensor known in the art, and can include a plurality of sensors positioned within or around the detection area of the system. In at least one embodiment, the sensors may be mounted on a movable platform that moves around the individual being scanned.

Upon detection of a temperature increase within the detection area, the alarm 835 is triggered to indicate the presence of metal. The alarm can be an audio alarm, a visual alarm, an audiovisual alarm, a tactile alarm, etc. The alarm 835 alerts an operator of the detection system to the presence of metal so that a search of the individual or other action can be taken prior to allowing the individual to enter the event/ building. In one embodiment, the system uses a temperature increase threshold to determine whether to trigger the alarm 835. The temperature increase threshold can be relative to an ambient environmental temperature and/or relative to a body temperature (i.e., 98.6 degrees Fahrenheit (F)) of the individual being tested. For example, on a day when the ambient temperature is 70 degrees F., it would be expected that no part of an individual being tested should exceed his/her body temperature, and the temperature threshold for triggering the alarm 835 can be 100 degrees F., 102 degrees F., 105 degrees F., etc. On a day when the ambient temperature is 110 degrees F., it would be expected that no part of the individual being tested should exceed 110 degrees F., and the temperature threshold for triggering the alarm 835 can be 112 degrees F., 115 degrees F., etc.

In an embodiment in which the temperature threshold is based at least in part on ambient environmental temperature, the temperature threshold is dynamic such that it changes as the ambient temperature changes. For example, the temperature threshold can be set to a predetermined number of degrees greater than the ambient temperature, where the predetermined number of degrees can be 1 degree, 2 degrees, 5 degrees, 10 degrees, etc. In one embodiment, the system is configured to determine the temperature threshold based on the greater of the individual's body temperature and the ambient environmental temperature.

The processor 805 is used to control the induction detector system 800, and can be any type of computer processor or controller known in the art. For example, the processor can be used to run an algorithm to dynamically determine a temperature threshold for triggering the alarm 835 based on ambient temperature of the environment in which the detection system is located. The processor 805 can also compare a temperature detected by the temperature sensor 830 to the temperature threshold and trigger the alarm 835 if the temperature threshold is exceeded. The processor 805 can also be used to calibrate the temperature sensor 830, to control and interact with the memory 810, to control and interact with the transceiver 815, and to control and interact with the interface 820.

The memory 810 can be any type of computer memory or storage known in the art. The memory 810 can be used to store system information such as a temperature threshold, an algorithm for dynamically adjusting the temperature threshold, an algorithm for determining whether to activate the alarm 835, an operating system, a log of detected data, etc. The algorithms can be stored as computer-readable instructions on the memory 810, and the memory 810 can be a non-transitory computer-readable medium that is accessible by the processor 805.

The transceiver 815 can be any type of receiving and/or transmitting device known in the art. The transceiver 815 can be used to transmit an alert to a remote location upon detection of metal by the system. The transceiver 815 can also be used to receive programming instructions, temperature threshold data, algorithms, etc. from a remote location through a network such as the Internet. The interface 820 includes one or more components that allow an operator to interact with the system 800. For example, the interface 820 can include a display, a mouse, a keyboard, ports, a microphone, a speaker, switches or other manual system controls, etc. The interface 820 allows the operator to control the system, program the system, reset the system, perform troubleshooting on the system, etc.

In one embodiment, the induction detector system also includes one or more cameras. The one or more cameras can be used to capture one or more images of all individuals who are tested by the system. Alternatively, the one or more cameras can be used to capture one or more images only of the individuals that trigger the alarm 835. The captured images can be stored in the memory 810, presented on the interface 820, and/or sent to a remote location using the transceiver 815.

As one example implementation, the induction detection system is implemented as a stationary system that includes a detection system housing in the form of a gate, arch, tunnel, chamber, etc. that a user enters or walks through prior to entering a building or event. In one embodiment, the detection system is partially or entirely surrounded by an electromagnetic radiation shield to ensure that any generated radiation remains in the detection area of the system and does not contact or affect bystanders that are proximate to the system. Additionally, the user can be asked to remove all metallic objects from his/her person prior to entering the housing of the induction detector system, similar to the process of going through a metal detector at an airport. The detection system can also be accompanied by warnings to warn individuals of possible health issues that can occur due to metallic implants. In one embodiment, the user is asked to stand still at a specific location (i.e., a detection area) within the housing while the individual is tested for metal. In one implementation, one or more walls of the housing surround the user and have temperature sensors incorporated therein to detect any generated heat. The one or more walls can be stationary or they may move relative to the individual to perform detection on all areas of the individual. Alternatively, instead of walls, one or more arms or other projections can be mounted on a movable platform and used to scan the individual's entire body for generated heat that results from the introduction of the electromagnetic radiation into the detection area.

Detected temperatures resulting from the scanning of the individual's body are compared to a temperature threshold, which can be set as an outright temperature (such as X degrees), or as a temperature change relative to the individual's body temperature or the ambient environmental temperature. For example, if set as an outright temperature, the temperature threshold hold may be 90 degrees, 100 degrees, 105 degrees, etc. If the temperature threshold is set as a temperature relative to body temperature or ambient temperature, the threshold may be 1 degree, 2 degrees, 5 degrees, 10 degrees, 25 degrees, etc. If the temperature threshold is exceeded, the alarm is triggered. As a result of the alarm, the individual may be searched and/or refused entry to the building or event.

As another example implementation, the induction detector system 800 of FIG. 8 can also be formed as a portable detection unit that can be used to detect metal on an individual's person, metal behind or within a wall, etc. The portable induction detector system can include a battery to power the system, or the system can be powered through a wall outlet or other power source. The portable detection unit can be a handheld wand in one embodiment, which is used to scan an individual for metal prior to allowing the individual to enter a building or event. For example, the wand can use an electromagnetic source (e.g., the electromagnetic radiation source 825) to induce heat in metallic objects such as knives or guns carried by the individual being tested. One or more temperature sensors on the wand are used to detect the temperature on or near the individual and to compare the detected temperature to a temperature threshold as described herein. If the temperature threshold is exceeded, an alarm is triggered and the operator is made aware that the individual being tested is carrying metal. In alternative embodiments, form factors other than a wand can also be used to implement the portable system.

As discussed above, the portable induction detection system can also be used to determine whether there is metal within or behind a wall. For example, a construction crew can use the portable induction detection system to determine the location of metallic pipes and/or wires within a wall using the techniques described herein. The construction crew can use this information to access the pipes/wires with accuracy, thereby causing minimal damage to the wall. The construction crew can also use this information to avoid the pipes/wires within the wall so that leaks, electrical hazards, and other problems are avoided. In another embodiment, the portable induction detection system can be used in military or police operations within a building to detect bombs, guns, artillery shells, and other potentially hazardous material that are inside of a wall or adjacent to the wall. In such embodiments, the heat sensor(s) of the portable induction detection system can be positioned adjacent to the wall to detect heat generated within the wall or on the other side of the wall.

In one embodiment, the electromagnetic radiation source of the induction detection systems described herein is adjustable such that varying amounts of heat can be generated in metallic objects. For example, a lower magnitude of electromagnetic radiation can be used in a stationary/portable detection system that is used on individuals to prevent the individuals from being burned due to excessive generated heat. Similarly, in an induction detection system used to detect metallic objects within or behind a wall, the electromagnetic radiation may be increased to generate higher temperatures which can be detected at a further distance from the system. Additionally, in the case of a plastic gun with metallic ammunition that is positioned behind a wall, the increased electromagnetic radiation can be used to excessively heat the metallic ammunition and at least partially melt the plastic gun, rendering it unusable. Similarly, the increased heating of a metallic gun, bomb, etc. behind a wall may make the weapon more difficult to use without the user getting burned.

In another illustrative embodiment, the temperature sensor(s) of the induction detection system can be used to detect motion behind or within a wall. As an example, an array of temperature sensors can be positioned on or adjacent to the wall, and the processor of the system can use the detected temperatures from each of the sensors to determine if the generated heat is moving or if it remains stationary. For example, a first temperature sensor can detect an increased temperature at a first location at a first time, and a second temperature sensor can detect an increased temperature at a second location at a second time. If, at the second time, the heat detected by the first temperature sensor at the first location has dissipated, such dissipation can be indicative of movement of a metallic object from the first location to the second location. The movement can be indicative of a person being present on the other side of the wall, and is used to determine an appropriate course of action. If, at the second time, the heat detected by the first temperature sensor remains, this can be indicative of a large metal object through which the heat resulting from the electromagnetic radiation is spreading.

As discussed above, in an illustrative embodiment, the electromagnetic radiation intensity can be controlled such that excessive heating of metallic objects does not occur. Such excessive heating could potentially cause damage to individuals and/or their property. In an alternative implementation, a high intensity and/or high frequency radiation source can be used to intentionally cause excessive heating of nearby metallic objects. For example, in the context of a standoff, military operation, hostage situation, etc. it may be desirable to attempt to excessively heat the metallic objects associated with a perpetrator in an effort to physically harm them and/or render their weapons unusable. For example, a metallic bullet can be heated to cause melting of plastic portions of a firearm, rendering the firearm unable to be fired. Similarly, a knife/firearm can be heated such that the perpetrator is unable to handle the weapon.

In another embodiment, a frequency and/or intensity of the electromagnetic radiation source can be continually cycled to varying magnitudes (e.g., high/low/high/low). Such cycling can help to offset the effect of a radiation shield used to block radiation, such as a graphite opaque shield. Specifically, cycling the frequency and/or intensity increases the likelihood of using a radiation signal that is not able to be blocked by the shield.

The embodiments described herein can also be used to detect metallic objects in luggage and shipping packages. For example, in situations where ferromagnetic metals are not supposed to be present in luggage or parcels, the presently described embodiments can be used to detect any ferromagnetic metals and generate an alert responsive to the detection. Specifically, electromagnetic radiation can be directed at the luggage/parcels and a temperature sensor used to detect any increase in temperature that occurs via induction heating as a result of the directed radiation. An increase in temperature indicates the presence of a ferromagnetic metal, which results in an alert to a system operator, who can then perform additional inspection of the luggage/parcel. A similar process can be used to detect hidden cameras, phones, microphones, etc. that include ferromagnetic metal. Specifically, radiation can be directed at an individual that may be carrying such surveillance items, and the resulting induction heating of the surveillance items can indicate their presence and/or render them unusable.

Another embodiment is directed to an induction system for mold remediation. Mold within a dwelling or other structure can cause serious health issues such as nasal and sinus congestion, respiratory problems, throat irritation, eye irritation, allergic reaction, etc. Mold is often found in between walls and in other areas in which the mold is not readily visible. Traditional techniques to remediate the mold involve tearing down the wall, removing the mold and/or materials covered with mold, and rebuilding the wall. Such a process is time consuming, expensive, and inconvenient to a homeowner.

Described herein is a system and method that utilizes induction heating to kill the mold. In an illustrative embodiment, induction heating is used to heat the mold to a temperature of ~160° Fahrenheit (F) for approximately 30 minutes to destroy the mold. If the mold is on an exposed (i.e., accessible) surface, a ferromagnetic plate or other material with ferromagnetic particles can be positioned on the mold, and an electromagnetic radiation source can be activated to direct radiation toward the ferromagnetic material. The material becomes hot through induction and is maintained at a desired temperature for a predetermined amount of time to remediate the mold.

However, as noted above, mold often accumulates in between walls and in other difficult to access areas. In order to use induction heating to remediate the mold in such scenarios, ferromagnetic particles are positioned near the mold and heated. In one embodiment, an expandable foam or a spray insulation is impregnated with ferromagnetic particles. In such an implementation, a small hole can be placed on one side of a wall and the expandable foam or spray insulation can be placed in between the walls through the hole. The expandable foam or spray insulation will expand to fill the space between the walls such that it is in contact with the mold. The ferromagnetic particles can also be incorporated into fiberglass (or other) insulation that is installed between the walls. An electromagnetic radiation source is activated and the radiation is directed toward the ferromagnetic particles in between the walls. The ferromagnetic particles become hot through induction, and the radiation is controlled to maintain the particles at a desired temperature for a predetermined amount of time to remediate the mold.

In another embodiment, ferromagnetic particles are impregnated into a wall board such as a gypsum board, a cement board, etc. that is used to form the walls of a structure. As a result, in the event of mold, there is no need to drill a hole in the wall or tear down the wall to perform heat remediation. Rather, electromagnetic radiation is directed to the portion(s) of the wall where mold is suspected, and the wall is heated to and maintained at a desired temperature to perform the remediation.

In another embodiment, a ferromagnetic sheet is used to cover all or a portion of the rear side of a wall board (i.e., the side of the wall board that is not visible after installation thereof). In such an embodiment, the ferromagnetic sheet may include openings to reduce the amount of material used. The openings can be sized such that the entire wallboard is still able to be heated through induction heating of the sheet. In such an embodiment, only a portion of the rear side of the wall board is in contact with the ferromagnetic sheet, and the portion can be 40%, 50%, 60%, 80%, etc. Alternatively, instead of a ferromagnetic sheet, a ferromagnetic mesh (e.g., a screen) can be used to cover the rear side of the wall board. In another embodiment, the ferromagnetic sheet or mesh can be incorporated into an interior of the wall board such that the sheet/mesh is not visible. Such an implementation can improve the structural integrity of the wall board and better enable both sides of the wall board to be heated through induction such that mold remediation can readily be performed on either side of the wall through induction heating.

Figure 9:
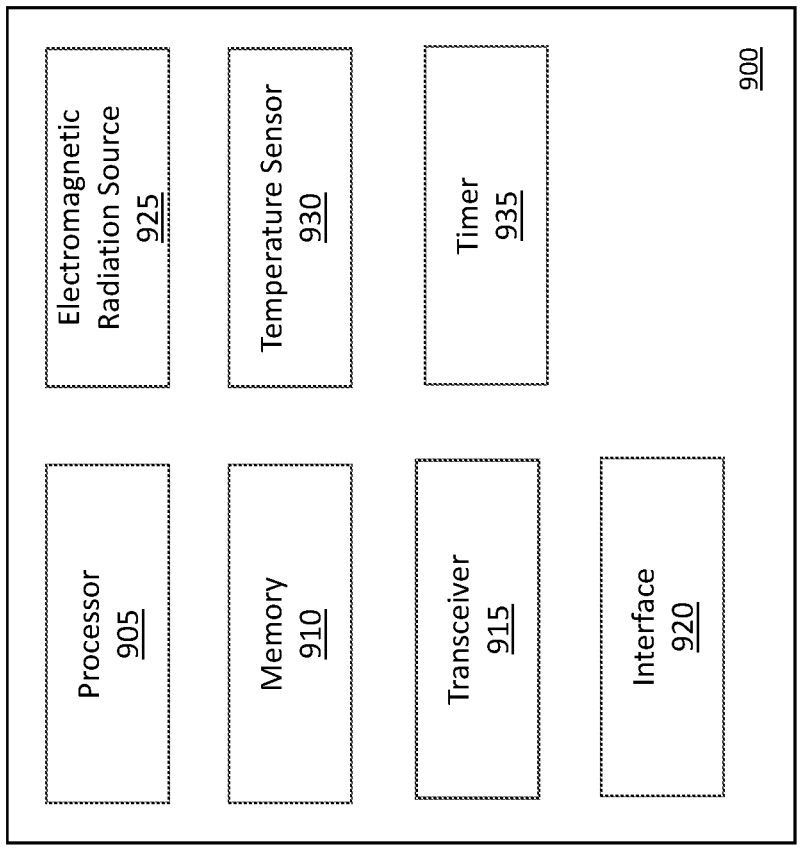
FIG. 9 is a block diagram of an induction system for mold remediation in accordance with an illustrative embodiment.

FIG. 9 is a block diagram of an induction system for mold remediation in accordance with an illustrative embodiment. The system 900 includes a processor 905, a memory 910, a transceiver 915, an interface 920, an electromagnetic radiation source 925, a temperature sensor 930, and a timer 935. In alternative embodiments, the induction system 900 may include fewer, additional, and/or different components. In an illustrative embodiment, the induction system can be implemented as a portable unit that can be moved into and throughout a building to perform mold remediation. The induction mold remediation system can also be implemented as a handheld unit that can be temporarily mounted to a wallboard to perform mold remediation.

The processor 905 is used to control the induction system for mold remediation 900. The processor 905 can be any type of computer processor or controller known in the art. The memory 910 can be any type of computer memory or storage known in the art. The memory 910 can be used to store system information such as a desired temperature at which to remediate mold, which can be ~140°, ~150°, ~160°, ~170°, etc. The memory 910 can also be used to store a time period for which the desired temperature is to be maintained to remediate the mold, such as 30 minutes, 1 hour, 2 hours, 3 hours, etc. The memory 910 can further be used to store one or more algorithms for controlling the electromagnetic radiation source 925 to reach and maintain the desired temperature. The algorithms can be stored as computer-readable instructions on the memory 910, and the memory 910 can be a non-transitory computer-readable medium that is accessible by the processor 905.

The transceiver 915 can be any type of receiving and/or transmitting device known in the art. The transceiver 915 can be used to transmit information to a remote device such as a smart phone, laptop computer, remote server, etc. The transmitted information can include data regarding the status of mold remediation, the maximum detected temperature at the mold remediation site, the duration of induction heating, the variation in temperature throughout the remediation process, etc. The transceiver 915 can also be used to receive programming instructions, desired temperature data, a time period or duration for which the remediation is to be performed, algorithms, etc. from a remote device through a network such as the Internet. The interface 920 includes one or more components that allow an operator to interact with the system 900. For example, the interface 920 can include a display, a mouse, a keyboard, ports, a microphone, a speaker, switches or other manual system controls, etc. The interface 920 allows the operator to control the system, program the system, reset the system, perform troubleshooting on the system, etc.

The electromagnetic radiation source 925 can be any type of electromagnetic radiation generating system known in the art. In an illustrative embodiment, the electromagnetic radiation source 925 is used to direct electromagnetic radiation at the ferromagnetic material (e.g., embedded particles, sheets, mesh, etc.) that is on or within a wall board. In another illustrative embodiment, the electromagnetic radiation source 925 is dynamically controlled to achieve and maintain the desired temperature for the desired duration of time. Dynamic control allows the system 900 to achieve and maintain the temperature in varying ambient conditions. For example, a greater amount of radiation may be used to maintain the desired temperature in a colder environment.

The temperature sensor 930 is used to detect the temperature of the wall board that results from the interaction of the ferromagnetic material and the electromagnetic radiation. The temperature sensor 930 can be any of type of temperature/thermal sensor known in the art, and can include a plurality of sensors positioned within or around the system 900. In at least one embodiment, the temperature sensor (or sensors) 930 is positioned on the side of the wall board upon which mold is being remediated. In one embodiment in which mold is between walls, the temperature sensor 930 can be placed between the walls through a small hole that is drilled into the wall. In an alternative embodiment in which no hole/opening is made in the wall, the temperature sensor 930 can be placed on the opposite side of the wall board from where the mold is being remediated (i.e., on the accessible side of the wall board). In such an embodiment, the system 900 is configured to mathematically determine the temperature on the inaccessible side of the wall board based on the temperature of the accessible side of the wall board. The mathematical determination is based at least in part on the heat conductivity property of the wall board, which is based on the type of material that makes up the wall board and the thickness of the wall board. The timer 935 can be any type of timer/clock known in the art, and is used to keep track of the duration of mold remediation to ensure that the wall board has been heated for an appropriate amount of time.

In an illustrative embodiment, the processor 905 is configured to execute a mold remediation algorithm that is stored in the memory 910. The mold remediation algorithm is used to dynamically control the electromagnetic radiation source 925 to achieve a desired temperature to remediate the mold. As discussed, the amount of electromagnetic radiation used to achieve the desired temperature varies based on ambient temperature and particulars of the wall board and structure in which the mold is located. The processor 905 also uses the temperature sensor 930 to monitor the temperature and to ensure that the desired temperature is maintained for the desired duration of time. The processor 905 also uses the timer 935 to monitor the time duration.

In addition to mold remediation, the embodiments described herein can be used in any application in which it is desirable to heat one side of a surface, but not the other. Unlike use of a heat gun or other conduction-based heating system, induction heating is controllable through placement of the ferromagnetic material heats up in response to radiation. For example, it may be desirable to heat only a rear side of a wall to protect a valuable painting or other artwork that is displayed on a front side of the wall. The rear side of the wall can be heated by placing ferromagnetic material on or adjacent to the rear side of the wall and passing electromagnetic radiation through the ferromagnetic material. As a result, there is little or no heat experienced by the front side of the wall. This technique can be used in any situation in which is desirable to heat one side of a surface but not the other.

In another illustrative embodiment, induction heating can be used to activate and/or cure an adhesive substance to bond materials together. For example, various types of flooring materials are installed via an adhesive. However, traditional installations are limited by the small amount of adhesive that can be applied at a given time to prevent unintentional setting. For example, it is typically not possible to apply adhesive to an entire floor and then install flooring over the entire floor because the installers are unable to avoid contact with the adhesive, which is messy and reduces the effectiveness of the adhesive. Additionally, the adhesive may begin to set up (i.e., harden) before the installation is complete, which necessitates the difficult process of removing the set adhesive and reapplying new adhesive. As a result, a typical installation involves applying adhesive to a small portion of the floor and then quickly (i.e., prior to the adhesive setting) installing the flooring material to the small portion of the floor. This time consuming process is repeated until the entire floor is covered.

The difficulties associated with a traditional flooring installation can be avoided by using a heat activated adhesive and an induction heating system. Any type of heat activated or heat cured adhesive known in the art may be used such as epoxy, laminating adhesive, water-based adhesive, polyurethane, emulsion adhesive, hot melt adhesive, etc. In one embodiment, ferromagnetic particles are incorporated into the heat activated adhesive and, upon application of electromagnetic radiation from an EM source, the ferromagnetic particles are heated, thereby causing the adhesive to activate at set. The ferromagnetic particles can be nanoparticles, micro-particles, etc. In an alternative embodiment, ferromagnetic sheets can be applied over the installed flooring and the sheets can be heated with EM radiation to activate an adhesive applied underneath the installed flooring.

As an example, a heat activated adhesive is applied to a subfloor onto which flooring is to be installed. The application of the adhesive can be performed using any techniques known in the art such as spraying, rolling, etc. The flooring is then installed on top of the heat activated adhesive using any techniques known in the art. An induction heating system is used to activate the adhesive to bond the installed flooring to the subfloor. The induction heating system can include one or more of a processor, memory, transceiver, interface, electromagnetic radiation source, and a temperature sensor.

In an illustrative embodiment, the electromagnetic radiation source of the induction heating system is used to activate the adhesive by directing radiation at ferromagnetic particles embedded in the adhesive. Alternatively, the adhesive may not include particles and ferromagnetic sheets (or other ferromagnetic material) can be temporarily applied over the installed flooring. In such an implementation, the radiation is directed to the sheets (or other ferromagnetic material), which causes them to heat up. The heat is transferred from the sheets to the installed flooring and to the heat activated adhesive. As a result, the adhesive is heated and activated, which bonds the flooring to the subfloor.

A temperature sensor of the induction heating system is used to directly or indirectly detect the temperature of the heat cured adhesive to ensure that the proper temperature for activation/curing is achieved. The system can also include a timer that is used to monitor the amount of time which the proper temperature is maintained. For example, some heat activated adhesives need to be heated for a specified duration of time to ensure proper activation and curing. The processor of the system is used to control the various components to ensure that the specified temperature and time duration is used.

It is noted that the installation of flooring is just one example for the use of an induction heating system to activate an adhesive, and that the application is not so limited. In alternative embodiments, the induction heating system can be used to activate a heat activated adhesive for any other application such as component assembly, hanging objects on a wall, woodworking, etc. In another embodiment, the induction heating system can be used to perform soldering to adhere materials to one another. For example, electromagnetic radiation can be directed from an EM source to solder (e.g., lead, tin, copper, etc.) to heat and melt the solder, which can then be used to adhere materials as known in the art. If the solder material is not ferromagnetic, ferromagnetic particles can be implanted into the solder material such that the radiation heats the implanted particles, thereby heating and melting the solder.

The induction heating systems described herein can also be used to detect wires and/or pipes behind walls. The wires and/or pipes can be made from ferromagnetic materials and/or can be wrapped with a ferromagnetic material or have ferromagnetic particles incorporated therein. Specifically, EM radiation is directed at a wall and a temperature sensor is used to detect whether there is a temperature increase behind the wall. The temperature sensor can be used on the accessible side of the wall or placed behind the wall via a small hole in the wall. The EM radiation causes the pipe/wire to heat up, which is detected by the temperature sensor and indicative that a pipe/wire is present.

The induction heating systems can also be used to provide heat to ferromagnetic objects such as a metallic structure surrounding a beehive during the winter to keep the beehive warm. The induction systems can similarly be used to heat water pipes to prevent them from freezing, to heat a metallic shed, a fish pond, or other structure, etc. Notably, the induction heating systems can be used in any application in which wireless heating is desired. For example, it may be undesirable to run electrical wires into a fish pond. Induction heating can be used to heat the fish pond without the need to run wires. For example, one or more ferromagnetic rods can be placed into the water and heated via induction. The rods then pass the heat to the water in the pond via conduction, heating the water and preventing it from freezing. A partial or complete covering over the pond can also be used. The covering can be made of ferromagnetic material, which is heated by induction, thereby heating the water through conduction.

As discussed above, the induction heating systems can be used in any application in which wireless heating is desired. Induction heating can be used to heat a blanket, a bed, or a portion of a bed. For example, a blanket containing ferromagnetic particles can be placed on or under a bed and heated with induction heating. Doghouses, sheds, storage containers, etc. that are not wired for electricity can also be heated through induction, as long as an electromagnetic radiation source can be activated in proximity to the object being heated. In one embodiment, the electromagnetic radiation source is battery-operated, and can be used off of the electrical grid to provide induction heating.

It should be understood that the disclosed embodiments have been described to provide the best illustration of the principles of the subject matter and its practical application to thereby enable one of ordinary skill in the art to utilize the system in various embodiments and with various modifications as are suited to the particular use contemplated.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A mold remediation system comprising:
   a processor;
   an electromagnetic radiation source in communication with the processor, wherein the electromagnetic radiation source is configured to emit radiation to heat a ferromagnetic material in or adjacent to a wall board upon which mold is located; and
   a temperature sensor in communication with the processor, wherein the temperature sensor is configured to detect a temperature of the wall board;
   wherein the processor is configured to compare the temperature of the wall board to a desired temperature to perform mold remediation.

2. The system of claim 1, wherein the ferromagnetic material comprises ferromagnetic particles embedded within the wall board.

3. The system of claim 1, wherein the ferromagnetic material comprises a ferromagnetic sheet adhered to at least a portion of the wall board.

4. The system of claim 1, wherein the ferromagnetic material comprises a ferromagnetic mesh adhered to at least a portion of the wall board.

5. The system of claim 1, further comprising a timer, wherein the processor uses the timer to monitor a time duration for which the desired temperature is maintained.

6. The system of claim 5, wherein the processor is configured to compare the time duration to a desired time duration to determine whether mold remediation is complete.

7. The system of claim 6, wherein the processor is configured to turn off the electromagnetic radiation source responsive to a determination that the mold remediation is complete.

8. The system of claim 1, wherein the processor is configured to control an amount of the electromagnetic radiation emitted by the electromagnetic radiation source based at least in part on the desired temperature.

9. The system of claim 8, wherein the processor controls the amount of the electromagnetic radiation based at least in part on an ambient temperature of the wall board.

10. The system of claim 1, further comprising a housing that is configured to mount to the wall board, wherein the housing is configured to house at least the processor and the electromagnetic radiation source.

11. The system of claim 1, wherein the temperature sensor comprises a plurality of temperature sensors positioned in an array.

12. The system of claim 11, wherein the processor is configured to monitor the array of temperature sensors, and wherein the determined temperature of the wall board comprises a lowest temperature detected from the array of temperature sensors.

13. The system of claim 1, wherein the ferromagnetic material is incorporated into insulation that is adjacent to the wall board.

14. The system of claim 1, wherein the ferromagnetic material is incorporated into an expandable foam that is adjacent to the wall board.

15. A method for performing mold remediation, the method comprising:
    emitting, by an electromagnetic radiation source, radiation to heat a ferromagnetic material in or adjacent to a wall board upon which mold is located;
    detecting, by a temperature sensor, a temperature of the wall board; and
    comparing, by a processor in communication with the electromagnetic radiation source and the temperature sensor, the temperature of the wall board to a desired temperature to perform mold remediation.

16. The method of claim 15, further comprising controlling, by the processor, an amount of the electromagnetic radiation emitted by the electromagnetic radiation source based at least in part on the desired temperature.

17. The method of claim 15, further comprising controlling, by the processor, an amount of the electromagnetic radiation based at least in part on an ambient temperature of the wall board.

18. The method of claim 15, further comprising using a timer to monitor a time duration for which the desired temperature is maintained.

19. The method of claim 18, further comprising comparing, by the processor, the time duration to a desired time duration to determine whether mold remediation is complete.

20. The method of claim 19, further comprising turning off the electromagnetic radiation source, by the processor, responsive to a determination that the mold remediation is complete.

* * * * *